US009447472B2

(12) United States Patent
Kanai et al.

(10) Patent No.: US 9,447,472 B2
(45) Date of Patent: Sep. 20, 2016

(54) METHOD FOR ASSESSING RISK OF HEPATOCELLULAR CARCINOMA

(75) Inventors: Yae Kanai, Tokyo (JP); Eri Arai, Tokyo (JP); Ryo Nagashio, Tokyo (JP)

(73) Assignee: NATIONAL CANCER CENTER, Tokyo (JP)

( * ) Notice: Subject to any disclaimer, the term of this patent is extended or adjusted under 35 U.S.C. 154(b) by 34 days.

(21) Appl. No.: 13/982,039

(22) PCT Filed: Jan. 27, 2012

(86) PCT No.: PCT/JP2012/051803
§ 371 (c)(1),
(2), (4) Date: Sep. 23, 2013

(87) PCT Pub. No.: WO2012/102377
PCT Pub. Date: Aug. 2, 2012

(65) Prior Publication Data
US 2014/0017686 A1    Jan. 16, 2014

(30) Foreign Application Priority Data

Jan. 28, 2011  (JP) ................................ 2011-016695

(51) Int. Cl.
*C12Q 1/68* (2006.01)
*C07H 21/04* (2006.01)
(52) U.S. Cl.
CPC ....... *C12Q 1/6886* (2013.01); *C12Q 2600/154* (2013.01)
(58) Field of Classification Search
None
See application file for complete search history.

(56) References Cited

FOREIGN PATENT DOCUMENTS

JP         2010-148426 A     7/2010

OTHER PUBLICATIONS

Arai (Int J Cancer 2009 vol. 125 pp. 2854-2862).*
Duffy (European Journal of Cancer 2009 pp. 335-346).*
Feng (PNAS 2010 vol. 107 No. 19 pp. 8689-8694).*
Mei-Hwei Chang, MD et al., "Universal Hepatitis B Vaccination in Taiwan and the Incidence of Hepatocellular Carcinoma in Children", The New England Journal of Medicine, Jun. 1997, pp. 1855-1859, vol. 336, No. 26.
Yasuhito Tanaka et al., "A comparison of the molecular clock of hepatitis C virus in the United States and Japan predicts that hepatocellular carcinoma incidence in the United States will increase over the next two decades", PNAS, Nov. 2002, pp. 15584-15589, vol. 99, No. 24.
Peter A. Jones et al., "The Epigenomics of Cancer", Cell, Feb. 2007, pp. 683-692, vol. 128.
Shikhar Sharma et al., "Epigenetics in cancer", Carcinogenesis, 2009, pp. 27-36, vol. 31, No. 1.
Yae Kanai et al., "Alterations of DNA methylation associated with abnormalities of DNA methyltransferases in human cancers during transition from a precancerous to a malignant state", Carcinogenesis 2007, pp. 2434-2442, vol. 28, No. 12.
Yae Kanai, "Alterations of DNA methylation and clinicopathological diversity of human cancers", Pathology International, 2008, pp. 544-558, vol. 58.
Yae Kanai et al., "Aberrant DNA Methylation on Chromosome 16 Is an Early Event in Hepatocarcinogenesis", Jpn. J. Cancer Res., Dec. 1996, pp. 1210-1217, vol. 87.
Yutaka Kondo et al., "Genetic Instability and Aberrant DNA Methylation in Chronic Hepatitis and Cirrhosis—A Comprehensive Study of Loss of Heterozygosity and Microsatellite Instability at 39 Loci and DNA Hypermethylation on 8 CpG Islands in Microdissected Specimens From Patients With Hepatocellular Carcinoma", Hepatology, 2000, pp. 970-979, vol. 32.
H. Kaneto et al., "Detection of hypermethylation of the p16ink4a gene promoter in chronic hepatitis and cirrhosis associated with hepatitis B or C virus", Gut, 2001, pp. 372-377, vol. 48.
Yoshimasa Saito et al., "Overexpression of a splice variant of DNA methyltransferase 3b, DNMT3b4, associated with DNA hypomethylation on pericentromeric satellite regions during human hepatocarcinogenesis", PNAS, Jul. 2002, pp. 10060-10065, vol. 99, No. 15.
Yoshimasa Saito et al., "Increased Protein Expression of DNA Methyltransferase (DNMT) 1 is Significantly Correlated with the Malignant Potential and Poor Prognosis of Human Hepatocellular Carcinomas", Int. J. Cancer, 2003, pp. 527-532, vol. 105.
Yae Kanai, "Genome-wide DNA methylation profiles in precancerous conditions and cancers", Cancer Sci, Jan. 2010, pp. 36-45, vol. 101, No. 1.
Eri Arai et al., "DNA methylation profiles in precancerous tissue and cancers: carcinogenic risk estimation and prognostication based on DNA methylation status", Epigenomics 2010, pp. 467-481, vol. 2, No. 3.
Y. Sugino et al., "Epigenetic silencing of prostaglandin E receptor 2 (PTGER2) is associated with progression of neuroblastomas", Oncogene 2007, pp. 7401-7413, vol. 26.
K. Tanaka et al., "Frequent methylation-associated silencing of a candidate tumor-suppressor, CRABP1, in esophageal squamous-cell carcinoma", Oncogene 2007, pp. 6456-6468, vol. 26.

(Continued)

*Primary Examiner* — Amanda Haney
(74) *Attorney, Agent, or Firm* — Sughrue Mion, PLLC

(57) ABSTRACT

The present invention aims at providing a method for assessing risk of hepatocellular carcinoma with high sensitivity and specificity. Extracted were 30 regions containing 45 CpG sites which have DNA methylation levels significantly different between in normal liver tissue samples and in noncancerous liver tissue samples from patients with hepatocellular carcinoma. It was found that the noncancerous liver tissue samples from patients with HCC were able to be assessed for risk of hepatocellular carcinoma by setting cutoff values for distinguishing between the normal liver tissue samples and the noncancerous liver tissue samples from patients with HCC for the extracted 30 regions.

7 Claims, 15 Drawing Sheets

(56) References Cited

OTHER PUBLICATIONS

Eri Arai et al., "Genome-wide DNA methylation profiles in both precancerous conditions and clear cell renal cell carcinomas are correlated with malignant potential and patient outcome", Carcinogenesis 2009, pp. 214-221, vol. 30, No. 2.

Naotaka Nishiyama et al., "Genome-wide DNA methylation profiles in urothelial carcinomas and urothelia at the precancerous stage", Cancer Sci, Jan. 2010, pp. 231-240, vol. 101, No. 1.

Eri Arai et al., "Genome-wide DNA methylation profiles in liver tissue at the precancerous stage and in hepatocellular carcinoma", Int. J. Cancer 2009, pp. 2854-2862, vol. 125.

Kristin Wallace et al., "Association between folate levels and CpG island hypermethylation in normal colorectal mucosa", Cancer Prev Res (Phila), Dec. 2010, pp. 1552-1564, vol. 3, No. 12.

Christopher G. Bell et al., "Integrated Genetic and Epigenetic Analysis Identifies Haplotype-Specific Methylation in the FTO Type 2 Diabetes and Obesity Susceptibility Locus", PLoS One., Nov. 2010, e14040, vol. 5, No. 11.

Kristi Kerkel et al., "Altered DNA Methylation in Leukocytes with Trisomy 21", PLoS Genet., Nov. 2010, e1001212, vol. 6, No. 11.

Ryo Nagashio et al., "Carcinogenetic risk estimation based on quantification of DNA methylation levels in liver tissue at the precancerous stage", Int. J. Cancer, 2011, pp. 1170-1179, vol. 129.

Akiko Misawa et al., "Methylation-Associated Silencing of the Nuclear Receptor 112 Gene in Advanced-Type Neuroblastomas, Identified by Bacterial Artificial Chromosome Array-Based Methylated CpG Island Amplification", Cancer Res Nov. 2005, pp. 10233-10242, vol. 65.

International Search Report for PCT/JP2012/051803 dated Apr. 3, 2012.

* cited by examiner

METHOD FOR ASSESSING RISK OF HEPATOCELLULAR CARCINOMA

CROSS REFERENCE TO RELATED APPLICATIONS

This application is a National Stage of International Application No. PCT/JP2012/051803 filed Jan. 27, 2012, claiming priority based on Japanese Patent Application No. 2011-016695 filed Jan. 28, 2011, the contents of all of which are incorporated herein by reference in their entirety.

TECHNICAL FIELD

The present invention relates to a method for assessing risk of hepatocellular carcinoma, including detection of DNA methylation level. The present invention also relates to a primer used in the assessment method.

BACKGROUND ART

Hepatocellular carcinoma (HCC) is a world-widely known malignant tumor and found to be mainly caused by hepatitis virus infection. Accordingly, mass immunization has been implemented against hepatitis B virus (HBV), but mainly in Asia and Africa, it has been concerned that liver carcinogenesis associated with HBV will not be eradicated for many years in the future because the age of onset is 50 years or older (NPL 1). The spread of hepatitis C virus (HCV) in Japan which occurred in the 1950s and 1960s has caused rapid increase in incidence rate of HCC since the 1980s (NPL 2), and more recently, HCV infection has also spread rapidly in other countries including the United States.

As mentioned above, HCC usually develops in patients suffering from chronic hepatitis or cirrhosis associated with hepatitis virus infection. Moreover, in most of the patients, the function of liver is already decreased at the stage when HCC develops, and thus good treatment results cannot be expected unless the patients are diagnosed as cancer at an early stage. For this reason, surveillance (follow-up) of precancerous states such as chronic hepatitis and cirrhosis should be given priority, and close surveillance should be conducted particularly on patients with high risk of developing HCC to detect HCC at an early stage for surgical operations and the like, even if they are asymptomatic in clinical examination. However, close surveillance is excessively burdensome to patients having no risk of developing HCC. Accordingly, risk assessment of HCC development is essential for management of patients with chronic liver diseases such as chronic hepatitis and cirrhosis, and thus the development of its assessment has been needed.

On the other hand, alteration of DNA methylation is among the most consistent epigenetic changes observed in human multistep carcinogenesis (NPLs 3 to 4). Accumulated results of previous studies and the like suggest that alteration of DNA methylation is involved even in early and precancerous stages (NPLs 5 to 6). Also with respect to HCC development, it is found that alternation of DNA methylation, associated with splicing and/or expression abnormality of DNA methyltransferases, is already present in liver tissues with chronic hepatitis or cirrhosis, which are obtained from patients with HCC (NPLs 7 to 11).

Unlike expression of mRNA and proteins, which is susceptible to the microenvironment of cancer cells or precursor cells, alteration of DNA methylation is stably preserved in DNA double strands through covalent bonds, and is thus characterized in that even slight alteration in a precancerous state can be detected with high sensitivity. Accordingly, alteration of DNA methylation is expected to be the most suitable indicator for assessment of cancer risk (NPLs 12 to 13). In fact, the present inventors have identified 25 BAC clones, whose DNA methylation status is able to distinguish between normal liver tissues obtained from patients without HCC and noncancerous liver tissues obtained from patients with HCC in a learning cohort, by using BAC array-based methylated CpG island amplification (BAMCA, NPLs 13 and 19), which can provide an overview of the DNA methylation tendency of individual large regions in all chromosomes (NPL 18). The present inventors have proposed that the presence or absence of DNA methylation on such BAC clones is used as an indicator for assessing risk of developing HCC (PTL 1, NPLs 14 to 19).

However, with respect to the indicator, a large amount of genomic DNA is required for assessment of cancer risk because DNA inserted in the BAC clones has an average size of 170 kbp and methylated CpG sites with high diagnostic capability have not been identified. In addition, using BAMCA for such analysis requires high cost, making it difficult to apply the above indicator to practical diagnosis. Furthermore, in consideration of application to practical diagnosis, an indicator used for assessment of cancer risk may preferably have higher sensitivity and specificity (desirably, 100%) than an indicator using the BAC clones.

Thus, although there is a strong demand for a method for estimating risk of HCC with significantly high sensitivity and specificity, furthermore a method for estimating HCC risk with significantly high sensitivity and specificity while using a very small amount of genomic DNA from patients and lowering cost, such methods have not been put into practical use so far.

CITATION LIST

Patent Literature

[PTL 1] Japanese Unexamined Patent Application Publication No. 2010-148426

Non Patent Literature

[NPL 1] Chang M H et al., N. Engl. J. Med., 1997, volume 336, page 1855-9
[NPL 2] Tanaka Y et al., Proc. Natl. Acad. Sci. USA, 2002, volume 99, page 15584-9
[NPL 3] Jones P A et al., Cell, 2007, volume 128, page 683-92
[NPL 4] Sharma S et al., Carcinogenesis, 2009, volume 31, page 27-36
[NPL 5] Kanai Y et al., Carcinogenesis, 2007, volume 28, page 2434-42
[NPL 6] Kanai Y et al., Pathol. Int., 2008, volume 58, page 544-58
[NPL 7] Kanai Y et al., Jpn. J. Cancer Res., 1996, volume 87, page 1210-7
[NPL 8] Kondo Y et al., Hepatology, 2000, volume 32, page 970-9 [NPL 9] Kaneto H et al., Gut, 2001, volume 48, page 372-7
[NPL 10] Saito Y et al., Proc. Natl. Acad. Sci. USA, 2002, volume 99, page 10060-5
[NPL 11] Saito Y et al., Int. J. Cancer, 2003, volume 105, page 527-32 [NPL 12] Kanai Y et al., Cancer Sci., 2009, volume 101, page 36-45
[NPL 13] Arai E et al., Epigenomics, 2010, volume 2, page 467-81

[NPL 14] Misawa A et al., Cancer Res., 2005, volume 65, page 10233-42

[NPL 15] Sugino Y et al., Oncogene, 2007, volume 26, page 7401-13

[NPL 16] Tanaka K et al., Oncogene, 2007, volume 26, page 6456-68

[NPL 17] Arai E et al., Carcinogenesis, 2009, volume 30, page 214-21

[NPL 18] Arai E et al., Int. J. Cancer, 2009, volume 125, page 2854-62

[NPL 19] Nishiyama N et al., Cancer Sci., 2010, volume 101, page 231-40

SUMMARY OF INVENTION

Technical Problem

The present invention has been made in consideration of the above-described problems of the conventional techniques. An object of the present invention is to provide a method for assessing risk of hepatocellular carcinoma with high sensitivity and specificity.

Solution to Problem

The present inventors have earnestly studied in order to achieve the above object. As a result, the present inventors have reassessed, by pyrosequencing, the DNA methylation status at 203 XmaI/SmaI restriction endonuclease recognition sites on 25 BAC clone regions which indicate alteration of DNA methylation reflecting risk of developing hepatocellular carcinoma (HCC), in which the DNA methylation status has been already identified by BAMCA. Extracted were 30 regions containing 45 CpG sites that have DNA methylation levels significantly different between in the normal liver tissue samples and in the noncancerous liver tissue samples from patients with HCC. By setting a cutoff value for distinguishing between normal liver tissue samples and noncancerous liver tissue samples from patients with HCC for 30 extracted regions, the noncancerous liver tissue samples from patients with HCC can be determined to be in a high carcinogenic risk with high sensitivity and specificity.

In histopathology, the tissues sampled in biopsy are usually fixed in formalin and embedded in paraffin and DNA in the tissues is sheared, so that the reactions in PCR and pyrosequencing may be inhibited. Accordingly, the present inventors have found 15 regions among the 30 regions, which are less susceptible to reaction inhibition and can be assessed for risk of developing hepatocellular carcinoma with high sensitivity and specificity even when the tissues are fixed in formalin and embedded in paraffin.

The present inventors have found that there is a correlation between the number of regions satisfying the criteria based on the cutoff values for the noncancerous liver tissues from patients with HCC and prognosis (cancer-free survival rate and overall survival rate) of the same individual patients, thereby completing the present invention.

The present invention is specifically as follows.

(1) A method for assessing risk of hepatocellular carcinoma, including the following steps (a) to (c):

(a) preparing genomic DNA from liver tissue of a subject, (b) detecting a DNA methylation level of at least one site selected from the following group of CpG sites for the genomic DNA prepared in the step (a), (c) determining whether the subject is classified into a group of high cancer risk based on the DNA methylation level detected in the step (b), a group of CpG sites: CpG sites of Chromosome 1: 31,052,829, Chromosome 1: 31,093,130, Chromosome 1: 31,093,140, Chromosome 1: 31,093,145, Chromosome 1: 31,153,486, Chromosome 1: 31,153,497, Chromosome 1: 31,175,443, Chromosome 1: 47,677,654, Chromosome 1: 47,677,660, Chromosome 1: 47,677,663, Chromosome 1: 120,071,093, Chromosome 2: 235,289,886, Chromosome 5: 151,709,946, Chromosome 7: 44,315,806, Chromosome 7: 44,315,810, Chromosome 11: 3,617,363, Chromosome 11: 3,724,633, Chromosome 11: 3,724,650, Chromosome 11: 118,716,221, Chromosome 11: 118,798,005, Chromosome 11: 132,094,250, Chromosome 11: 132,094,254, Chromosome 11: 132,094,256, Chromosome 11: 132,094,259, Chromosome 11: 132,143,897, Chromosome 11: 132,186,602, Chromosome 12: 5,190,237, Chromosome 12: 5,239,770, Chromosome 12: 5,239,778, Chromosome 12: 50,601,217, Chromosome 12: 50,687,010, Chromosome 12: 50,687,013, Chromosome 12: 55,681,393, Chromosome 12: 55,732,381, Chromosome 12: 55,732,391, Chromosome 16: 4,538,435, Chromosome 16: 4,564,846, Chromosome 16: 4,642,726, Chromosome 16: 4,655,181, Chromosome 16: 4,672,961, Chromosome 19: 4,999,458, Chromosome 19: 4,999,468, Chromosome 19: 4,998,744, Chromosome 19: 5,099,166, and Chromosome 19: 5,099,171 located on the reference human genome sequence NCBI Build 36.1 assembly.

(2) The method according to (1), in which the step (b) is a step of detecting DNA methylation levels of all sites in the group of CpG sites for the genomic DNA prepared in the step (a).

(3) The method according to (1) or (2), in which the DNA methylation level is detected by pyrosequencing.

(4) An oligonucleotide according to any of the following (a) to (b), which have a length of at least 15 bases, for use in the method according to any of (1) to (3):

(a) an oligonucleotide which is a pair of primers designed to target at least one site selected from the group of CpG sites; and (b) an oligonucleotide which is a primer or probe that hybridizes to a base sequence containing at least one site selected from the group of CpG sites.

Advantageous Effects of Invention

According to the present invention, a method for assessing risk of hepatocellular carcinoma with high sensitivity and specificity can be provided. Further, in the present invention, the amount of genomic DNA from liver tissue which is required for the assessment is usually 1/500 to 1/17 and the cost is also usually 1/200 to 1/7 as compared with those required for assessment of risk of developing hepatocellular carcinoma and the like by BAMCA. Thus, according to the present invention, a method for estimating risk of HCC with significantly high sensitivity and specificity while using a relatively small amount of genomic DNA from patients to lower the cost.

DESCRIPTION OF EMBODIMENTS

Figure 1:
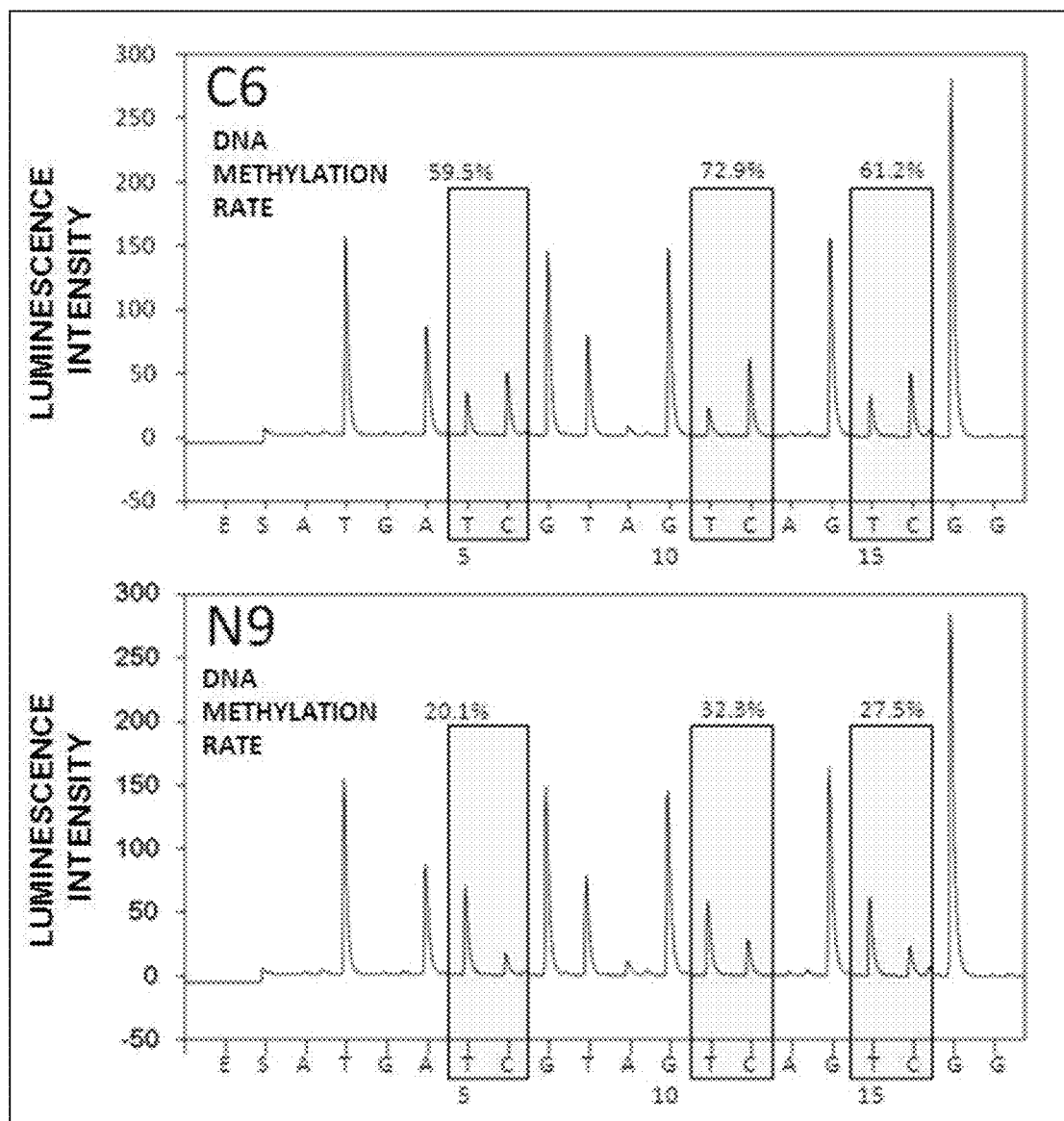
FIG. 1 shows pyrograms for examples of results of DNA methylation analysis by pyrosequencing. In the figure, "C6" shows a result of DNA methylation analysis for exon 1 of the FOXD2 gene (see chromosome 3: 47,677,654, -60, -63, Region 5 in Table 4) in a normal liver tissue sample from a patient without HCC, "N9" shows a result of DNA methylation analysis for exon 1 of the FOXD2 gene in a noncancerous liver tissue sample from a patient with HCC. The regions with gray columns indicate polymorphic sites after bisulfite modification. The horizontal axis indicates a dispensation order (order in which dNTP is added)(SEQ ID NO:121). The value (%) in the figure indicates DNA methylation level (rate) in each site.

The present invention provides a method for assessing risk of hepatocellular carcinoma, including the following steps (a) to (c):

(a) preparing genomic DNA from liver tissue of a subject;

(b) detecting DNA methylation level of at least one site selected from the following group of CpG sites for the genomic DNA prepared in the step (a); and (c) determining whether the subject is classified into a group of high cancer risk based on the DNA methylation level detected in the step (b).

The "hepatocellular carcinoma" in the present invention means primary hepatic cancer that develops from hepatocytes which substantially make up the liver, and is also referred to as HCC.

Examples of the "subject" in the present invention include, but are not particularly limited to, a healthy person, a person infected with hepatitis B, a person infected with hepatitis C, a patient with chronic hepatitis, a patient with cirrhosis, and a patient with hepatocellular carcinoma. The "risk of hepatocellular carcinoma" in the present invention means risk of developing hepatocellular carcinoma and risk of poor prognosis of hepatocellular carcinoma. Furthermore, the "CpG site" in the present invention means a site where cytosine (C) and guanine (G) are linked to each other through a phosphodiester bond (p), and the "DNA methylation" means a status where the carbon at position 5 of cytosine is methylated at the CpG site.

The method for "preparing genomic DNA from liver tissue" in the present invention is not particularly limited, and any well-known procedures can be appropriately selected and used. Examples of well-known procedures for preparing genomic DNA include a phenol-chloroform method (method for extracting DNA from liver tissue by denaturing proteins of the tissue with protease (proteinase K), a surfactant (SDS), and phenol, and causing precipitation of DNA with chloroform, ethanol, or the like), and DNA extraction methods using Clean Columns (registered trademark, produced by NexTec), Aqua Pure (registered trademark, produced by Bio-Rad Laboratories, Inc.), ZR Plant/Seed DNA Kit (produced by Zymo Research Corporation), AquaGenomic Solution (registered trademark, produced by MoBiTec GmbH), prepGEM (registered trademark, produced by ZyGEM), and BuccalQuick (registered trademark, produced by TrimGen Corporation).

Liver tissue from which genomic DNA is prepared by such methods is not particularly limited because risk of hepatocellular carcinoma can be assessed independently of the condition of liver tissue (hepatitis virus infection, inflammation, fibrosis, or the like, in the stage of chronic hepatitis and cirrhosis) and the distance from lesions of hepatocellular carcinoma according to the present invention, as illustrated below in Examples. Examples of such liver tissue include intact liver tissue sampled in biopsy and the like, liver tissue frozen after sampled in biopsy and the like, and liver tissue fixed in formalin and embedded in paraffin after sampled in biopsy and the like. With regard to these liver tissues, liver tissue frozen after sampled in biopsy and the like are desirably used because degradation of genomic DNA in liver tissue and the like are suppressed until the liver tissue is subjected to the assessment method of the present invention, and a bisulfite treatment and PCR can be carried out more efficiently in the step of detecting the DNA methylation level as described below.

As illustrated below in Examples, the present inventors have reassessed, by a pyrosequencing method, the DNA methylation status at 203 XmaI/SmaI restriction endonuclease recognition sites on 25 BAC clone regions that indicate alteration of DNA methylation reflecting risk of developing hepatocellular carcinoma (HCC), in which the DNA methylation status has been already identified by BAMCA, and have extracted 30 regions containing 45 CpG sites that have DNA methylation levels significantly different between normal liver tissue samples and noncancerous liver tissue samples from patients with HCC. It was shown that detection of DNA methylation levels of the CpG sites allows assessment of HCC risk. Specifically, the "CpG site" according to the present invention includes at least one site selected from the group consisting of the 45 CpG sites: Chromosome 1: 31,052,829, Chromosome 1: 31,093,130, Chromosome 1: 31,093,140, Chromosome 1: 31,093,145, Chromosome 1: 31,153,486, Chromosome 1: 31,153,497, Chromosome 1: 31,175,443, Chromosome 1: 47,677,654, Chromosome 1: 47,677,660, Chromosome 1: 47,677,663, Chromosome 1: 120,071,093, Chromosome 2: 235,289,886, Chromosome 5: 151,709,946, Chromosome 7: 44,315,806, Chromosome 7: 44,315,810, Chromosome 11: 3,617,363, Chromosome 11: 3,724,633, Chromosome 11: 3,724,650, Chromosome 11: 118,716,221, Chromosome 11: 118,798,005, Chromosome 11: 132,094,250, Chromosome 11: 132,094,254, Chromosome 11: 132,094,256, Chromosome 11: 132,094,259, Chromosome 11: 132,143,897, Chromosome 11: 132,186,602, Chromosome 12: 5,190,237, Chromosome 12: 5,239,770, Chromosome 12: 5,239,778, Chromosome 12: 50,601,217, Chromosome 12: 50,687,010, Chromosome 12: 50,687,013, Chromosome 12: 55,681,393, Chromosome 12: 55,732,381, Chromosome 12: 55,732,391, Chromosome 16: 4,538,435, Chromosome 16: 4,564,846, Chromosome 16: 4,642,726, Chromosome 16: 4,655,181, Chromosome 16: 4,672,961, Chromosome 19: 4,999,458, Chromosome 19: 4,999,468, Chromosome 19: 4,998,744, Chromosome 19: 5,099,166, and Chromosome 19: 5,099,171 located on the reference human genome sequence NCBI Build 36.1 assembly.

The number in the "Chromosome 1: 31,052,829" and the like indicate the location on the reference human genome sequence NCBI Build 36.1 assembly. As shown in Tables 1 to 3, these 45 CpG sites can be classified into 30 regions. Examples of the typical base sequences of such 30 regions include the base sequence described in SEQ ID NO: 91 as Region 1 containing the CpG site: Chromosome 1:31,052,829; the base sequence described in SEQ ID NO: 92 as Region 2 containing the CpG sites: Chromosome 1: 31,093,130, Chromosome 1: 31,093,140, and Chromosome 1: 31,093,145; the base sequence described in SEQ ID NO: 93 as Region 3 containing the CpG sites: Chromosome 1: 31,153,486, and Chromosome 1: 31,153,497; the base sequence described in SEQ ID NO: 94 as Region 4 containing the CpG site: Chromosome 1: 31,175,443; and the base sequence described in SEQ ID NO: 95 as Region 5 containing the CpG sites: Chromosome 1: 47,677,654, Chromosome 1: 47,677,660, and Chromosome 1: 47,677,663; the base sequence described in SEQ ID NO: 96 as Region 6 containing the CpG site: Chromosome 1: 120,071,093; the base sequence described in SEQ ID NO: 97 as Region 7 containing the CpG site: Chromosome 2: 235,289,886; the base sequence described in SEQ ID NO: 98 as Region 8 containing the CpG site: Chromosome 5: 151,709,946; the base sequence described in SEQ ID NO: 99 as Region 9 containing the CpG sites: Chromosome 7: 44,315,806, and Chromosome 7: 44,315,810; the base sequence described in SEQ ID NO: 100 as Region 10 containing the CpG site: Chromosome 11: 3,617,363; the base sequence described in SEQ ID NO: 101 as Region 11 containing the CpG sites: Chromosome 11: 3,724,633, and Chromosome 11: 3,724,650; the base sequence described in SEQ ID NO: 102 as Region 12 containing the CpG site: Chromosome 11: 118,716,221; the base sequence described in SEQ ID NO: 103 as Region 13 containing the CpG site: Chromosome 11: 118,798,005; the base sequence described in SEQ ID NO: 104 as Region 14 containing the CpG sites: Chromosome 11: 132,094,250, Chromosome 11: 132,094,254, Chromosome 11: 132,094,256, and Chromosome 11: 132,094,259; the base sequence described in SEQ ID NO: 105 as Region 15 containing the CpG site: Chromosome 11: 132,143,897;

the base sequence described in SEQ ID NO: 106 as Region 16 containing the CpG site: Chromosome 11: 132,186,602; the base sequence described in SEQ ID NO: 107 as Region 17 containing the CpG site: Chromosome 12: 5,190,237; the base sequence described in SEQ ID NO: 108 as Region 18 containing the CpG sites: Chromosome 12: 5,239,770, and Chromosome 12: 5,239,778; the base sequence described in SEQ ID NO: 109 as Region 19 containing the CpG site: Chromosome 12: 50,601,217; the base sequence described in SEQ ID NO: 110 as Region 20 containing the CpG sites: Chromosome 12: 50,687,010, and Chromosome 12: 50,687,013; the base sequence described in SEQ ID NO: 111 as Region 21 containing the CpG site: Chromosome 12: 55,681,393; the base sequence described in SEQ ID NO: 112 as Region 22 containing the CpG sites: Chromosome 12: 55,732,381, and Chromosome 12: 55,732,391; the base sequence described in SEQ ID NO: 113 as Region 23 containing the CpG site: Chromosome 16: 4,538,435; the base sequence described in SEQ ID NO: 114 as Region 24 containing the CpG site: Chromosome 16: 4,564,846; the base sequence described in SEQ ID NO: 115 as Region 25 containing the CpG site: Chromosome 16: 4,642,726; the base sequence described in SEQ ID NO: 116 as Region 26 containing the CpG site: Chromosome 16: 4,655,181; the base sequence described in SEQ ID NO: 117 as Region 27 containing the CpG site: Chromosome 16: 4,672,961; the base sequence described in SEQ ID NO: 118 as Region 28 containing the CpG sites: Chromosome 19: 4,999,458, and Chromosome 19: 4,999,468; the base sequence described in SEQ ID NO: 119 as Region 29 containing the CpG site: Chromosome 19: 4,998,744; and base sequence described in SEQ ID NO: 120 as Region 30 containing the CpG sites: Chromosome 19: 5,099,166, and Chromosome 19: 5,099,171.

In the present invention, the DNA methylation level of at least one of the 45 CpG sites may be detected. In order to further improve the sensitivity or specificity in assessment of cancer risk, however, it is preferred to detect the DNA methylation levels of the CpG sites, where the sensitivity and/or specificity are 100%: chromosome 16: 4,642,726, chromosome 16: 4,672,961, chromosome 19: 4,999,458, and 19 chromosome 19: 4,999,468; it is more preferred to detect the DNA methylation levels of the CpG sites, where the sensitivity and specificity are 100%: Chromosome 1: 31,175,443, Chromosome 1: 120,071,093, Chromosome 11: 3,617,363, Chromosome 11: 3,724,633, Chromosome 11: 3,724,650, Chromosome 11: 118,716,221, Chromosome 11: 132,094,250, Chromosome 11: 132,094,254, Chromosome 11: 132,094,256, Chromosome 11: 132,094,259, Chromosome 11: 132,143,897, Chromosome 12: 5,239,770, Chromosome 12: 5,239,778, Chromosome 12: 55,681,393, Chromosome 12: 55,732,381, Chromosome 12: 55,732,391, Chromosome 16: 4,538,435, Chromosome 16: 4,564,846, Chromosome 16: 4,642,726, Chromosome 16: 4,655,181, Chromosome 16: 4,672,961, Chromosome 19: 4,998,744, Chromosome 19: 4,999,458, and Chromosome 19: 4,999,468; and it is particularly preferred to detect the DNA methylation levels of all of the 45 CpG sites.

As illustrated below in Examples, it is also particularly preferred to detect the DNA methylation levels of all CpG sites in Regions 1 to 5, 14, 16, 18, 19, 21, 23, and 25 to 28 in order to assess the risk of hepatocellular carcinoma with high sensitivity and specificity as in the detection of the DNA methylation levels at all of the 45 CpG sites (the 30 regions), and further reduce the time and cost required for the assessment.

When genomic DNA from liver tissue fixed in formalin and embedded in paraffin is used, as illustrated below in Examples, it is preferred to detect the DNA methylation level of at least one of the CpG sites in Regions 1 to 5, 14, 16, 18, 19, 21, 23, and 25 to 28, and it is more preferred to detect the DNA methylation levels of all CpG sites in the Regions 1 to 5, 14, 16, 18, 19, 21, 23, and 25 to 28 in order to further improve the sensitivity or specificity in assessment of cancer risk.

A "method for detecting the DNA methylation level" in the present invention may be any method that can determine the DNA methylation level of a specific CpG site and can be performed by appropriately selecting a well-known method.

A first method is based on the following principle. First, the genomic DNA is treated with bisulfite. This bisulfite treatment converts unmethylated cytosine residues into uracil, while methylated cytosine residues remain unconverted (see Clark S J et al., Nucleic Acids Res., 1994, volume 22, page 2990-7.) In the following extension reaction (sequence reaction), uracil is expressed as thymine. Next, the bisulfite-treated genomic DNA is used as a template to amplify DNA containing at least one of the CpG sites. The amplified DNA is then dissociated into single strands. Subsequently, only one of single stranded DNA obtained by dissociation is separated. Then, the extension reaction is performed on each base from near the base of the CpG site, and pyrophosphoric acid generated during the reaction is caused to enzymatically emit light and the intensity of luminescence is determined. The intensity of luminescence from the methylated cytosine residue (luminescence intensity of cytosine) and the intensity of luminescence from the unmethylated cytosine residue (luminescence intensity of thymine), which are obtain in this way, are compared to calculate the DNA methylation level (%) of the CpG site, for example, based on the following formula.

DNA Methylation Level (%)=Luminescence Intensity of Cytosine×100/(Luminescence Intensity of Cytosine+Luminescence Intensity of Thymine)

Examples of the first method include pyrosequencing (registered trademark, Pyrosequencing) (see Anal. Biochem. (2000) 10: 103-110.)

In the first method, a primer used for amplification (polymerase chain reaction (PCR) primer (forward primer and reverse primer)) and a primer used for the extension reaction (sequencing primer) are designed based on the bisulfite-converted sequence near the base of the CpG site by well-known methods, for example, using Pyrosequencing Assay Design Software ver. 1.0 (produced by QIAGEN GmbH) as illustrated below in Examples. In the amplification, in order to overcome PCR bias in DNA methylation analysis, the annealing temperature and the like are desirably optimized as described in Shen L et al., Bio Techniques, 2007, volume 42, page 48-58, and Gao W et al., Carcinogenesis, 2008, volume 29, page 1901-10. Moreover, the "method for dissociating the amplified DNA into single strands and further separating only one of single strands" is not particularly limited, and examples of the method include a method for dissociating DNA amplified with a biotin-labeled primer into single strands and separating only one of single strands by using streptoavidin as illustrated below in Examples.

A second method is based on the following principle. First, the genomic DNA is treated with bisulfite. Subsequently, the bisulfite-treated genomic DNA is used as a template to amplify DNA containing at least one of the CpG sites using a primer with a T7 promoter. Next, the amplified DNA is transferred to RNA, followed by a base-specific cleavage reaction with RNAase. Then, a reaction product thus cleaved is subjected to a mass spectrometer for mass measurement.

The mass of the methylated cytosine residue (mass of cytosine) and the mass of the unmethylated cytosine residue (mass of thymine), which are obtain by the mass measurement, are compared to calculate the DNA methylation level of the CpG site.

Examples of the second method include DNA methylation analysis using a mass spectrometer (for example, see MassARRAY (registered trademark), Jurinke C et al., Mutat. Res., 2005, volume 573, page 83-95.)

A third method is based on the following principle. First, the genomic DNA is treated with bisulfite. Next, in a reaction system containing an intercalator which emits fluorescence when inserted between DNA double strands, the bisulfite-treated genomic DNA is used as a template to amplify a base sequence containing at least one of the CpG sites. Subsequently, the temperature of the reaction system is changed to detect variation in intensity of fluorescence emitted by the intercalator. The melting curve of the base sequence containing at least one of the CpG sites is compared with that of an amplified product with a methylated/unmethylated control analyte as a template to calculate the DNA methylation level of the CpG site.

Examples of the third method include methylation-sensitive high-resolution melting-curve analysis (see methylation-sensitive high resolution melting: MS-HRM, Wojdacz T K et al., Nat. Protoc., 2008, volume 3, page 1903-8.)

A fourth method is based on the following principle. First, the genomic DNA is treated with bisulfite. Next, a primer set capable of amplification when the CpG site is methylated and a primer set capable of amplification when the CpG site is not methylated are prepared. The bisulfite-treated genomic DNA is then used as a template to amplify a base sequence containing at least one of the CpG sites using each of these primers. Then, the amount of the obtained amplified product, i.e., the amount of the amplified product specific for the methylated CpG site and the amount of the amplified product specific for the unmethylated CpG site are compared to calculate the DNA methylation level of the CpG site.

Further, as another aspect of the fourth method, the genomic DNA is first treated with bisulfite. Next, an oligonucleotide probe having a base sequence which can be hybridized when the CpG site is methylated and labeled with a reporter fluorochrome and a quencher fluorochrome is prepared. Also, an oligonucleotide probe having a base sequence that can be hybridized when the CpG site is not methylated and labeled with a reporter fluorochrome different from the above reporter fluorochrome and a quencher fluorochrome is prepared. The oligonucleotide probe is then hybridized to the bisulfite-treated genomic DNA and further the genomic DNA to which the oligonucleotide probe is hybridized is used as a template to amplify a base sequence containing the CpG site. Then, degradation of the oligonucleotide probe associated with the amplification enables detection of fluorescence emitted by the reporter fluorochrome. The intensity of the fluorescence emitted by the reporter fluorochrome specific for a methylated cytosine CpG site and the intensity of the fluorescence emitted by the reporter fluorochrome specific for an unmethylated cytosine CpG site, which are detected in this way, are compared to calculate the DNA methylation level of the CpG site.

Examples of the fourth method include methylation-specific quantitative PCR (methylation-specific polymerase chain reaction (MS-PCR) using real-time quantitative PCR) such as the MethyLight assay using the TaqMan probe (registered trademark).

A fifth method is based on the following principle. First, the genomic DNA is treated with bisulfite. Next, a base sequence containing the bisulfite-converted CpG site was used as a template to directly perform a sequencing reaction. The fluorescence intensities of the determined base sequence, i.e., the fluorescence intensity from the methylated cytosine residue (fluorescence intensity of cytosine) and the fluorescence intensity from the unmethylated cytosine residue (fluorescence intensity of thymine) are compared to calculate the DNA methylation level of the CpG site.

Further, as another aspect of the fifth method, the genomic DNA is first treated with bisulfite. Subsequently, a base sequence containing the bisulfite-converted CpG site is cloned by PCR or the like. Then, more than one cloned product obtained is each sequenced. The number of cloned products having a base sequence specific for a methylated cytosine CpG site and the number of cloned products having a base sequence specific for an unmethylated cytosine CpG site are compared to calculate the DNA methylation level of the CpG site.

Examples of the fifth method include bisulfite direct sequencing and bisulfite cloning sequencing (see Kristensen L S et al., Clin. Chem., 2009, volume 55, page 1471-83.)

Although the methods that can be suitably used as the "method for detecting the DNA methylation level" of the present invention are illustrated above, the present invention is not limited thereto. Of these methods, pyrosequencing is preferably used in view of the best quantitative capability.

In the present invention, the criteria for determining whether the subject is classified into a group of high cancer risk based on the DNA methylation level detected in the step (b) are the cutoff values in the CpG sites or the regions as shown in Table 4. Specifically, in the step (C) according to the present invention, for example, when the DNA methylation level of Region 1 is detected, the detected DNA methylation level of lower than 25.5% allows the subject to be classified into a group of high cancer risk. For example, when the DNA methylation level of Region 11 is detected, the detected DNA methylation of higher than 95.7% allows the subject to be classified into a group of high cancer risk.

In the present invention, in order to further improve the sensitivity or specificity in assessment of hepatocellular carcinoma risk, as illustrated below in Examples, it is preferred to classify the subject into a group of cancer risk when there are 10 or more regions satisfying the criteria shown in Table 4 among the 30 regions, and it is more preferred to classify the subject into a group of high carcinogenic risk when there are 15 or more regions satisfying the criteria shown in Table 4.

In order to further improve the sensitivity or specificity in assessment of cancer risk and reduce the time and cost required for the assessment, it is more preferred to classify the subject into a group of cancer risk when there are 8 or more regions satisfying the criteria shown in Table 4 among Regions 1 to 5, 14, 16, 18, 19, 21, and 23, and 25 to 28.

In addition, when genomic DNA from liver tissue fixed in formalin and embedded in paraffin is used, in order to further improve the sensitivity or specificity in assessment of cancer risk, it is more preferred to classify the subject into a group of cancer risk when there are 8 or more regions satisfying the criteria shown in Table 4 among Regions 1 to 5, 14, 16, 18, 19, 21, 23, and 25 to 28, as illustrated below in Examples.

The present invention provides any oligonucleotides according to the following (a) to (b), which has a length of at least 15 bases, for use in the method for assessing risk of hepatocellular carcinoma:

(a) an oligonucleotide which is a pair of primers designed to target at least one site selected from the group of CpG sites, and (b) an oligonucleotide which is a primer or probe that hybridizes to a base sequence containing at least one site selected from the group of CpG sites.

Examples of the pair of primers designed to target at least one site selected from the group of CpG sites according to (a) include primers (polymerase chain reaction (PCR) primers (forward primers and reverse primers)) that can amplify DNA containing at least one site selected from the group of CpG sites, in which the CpG sites are bisulfite-converted. The primer can hybridize to each base sequence which is bisulfite-converted at both sides of at least one site selected from the group of CpG sites. Examples of the primer that hybridizes to a base sequence containing at least one site selected from the group of CpG sites according to (b) include primers (sequencing primers) that can perform the extension reaction on each base from near the bisulfite-converted CpG site. Moreover, examples of the probe that hybridizes to a base sequence containing at least one site selected from the group of CpG sites according to (b) include probes (what are called TaqMan probes (registered trademark)) that hybridizes to a base sequence containing the bisulfite-converted CpG site. The oligonucleotide that hybridizes to a specific base sequence has a base sequence complementary to the specific base sequence, but the base sequence may not be fully complementary to the specific base sequence as long as the oligonucleotide can hybridize. The sequence of these oligonucleotides can be appropriately designed based on the base sequence containing the CpG site bisulfite-converted or not-converted, by methods well-known to those skilled in the art, for example, using Pyrosequencing Assay Design Software ver. 1.0 (produced by QIAGEN GmbH) as illustrated below in Examples.

The oligonucleotide of the present invention is preferably a primer selected from the group consisting of the base sequences described in SEQ ID NOs: 1 to 90, as illustrated below in Examples (see Tables 1 and 2).

Furthermore, the present invention can also provide a kit for use in the method for assessing risk of hepatocellular carcinoma, including the oligonucleotide.

In a preparation of the oligonucleotide, the oligonucleotide may be labeled if necessary. For example, the biotin-labeled primer can be used in the case of detection by pyrosequencing, and the probe labeled with a reporter fluorochrome and a quencher fluorochrome can be used in the case of detection by the TaqMan probe method.

The kit of the present invention can contain preparations other than the preparation of the oligonucleotide. Examples of such preparations include reagents required for bisulfite conversion (for example, a solution of sodium bisulfite and the like), reagents required for PCR (for example, deoxyribonucleotide, thermostable DNA polymerase, and the like), reagents required for pyrosequencing (for example, ATP sulfurylase, adenosine-5'-phosphosulfate, luciferase, and luciferin for detection of pyrophoric acid, streptoavidin for separation of single stranded DNA, and the like), and reagents required for MS-HRM (for example, an intercalator which emits fluorescence when inserted between DNA double strands.) Examples of such preparations also include reagents required for detection of the label (for example, substrates and enzyme, positive control and negative control, or buffer solution used to dilute or wash samples (genomic DNA from liver tissues of subjects, and the like.) The kit can also include instructions for use.

EXAMPLES

Although the present invention will be described below in more detail based on Examples, the present invention is not limited to the following Examples. The samples and methods used in Examples are as follows.

<Patients and Tissue Samples>

As a learning cohort, normal liver tissue samples (C1 to C10) without noticeable histological findings were obtained from specimens surgically resected from 10 patients who suffered from other diseases than HCC and were negative for both HBV surface antigens (HBs-Ag) and anti-HCV antibodies (anti-HCV). These patients included seven men and three women, and the average age (±SD) was 58.4±9.7 years. Nine of these patients underwent partial hepatectomy for liver metastases of primary colon cancer and one patient underwent partial hepatectomy for liver metastases of gastrointestinal stromal tumor in the stomach at the National Cancer Center Hospital in Japan.

Further, 12 samples (N1 to N12) of noncancerous liver tissue were obtained from 12 patients who underwent partial hepatectomy for HCC. These patients included nine men and three women, and the average age was 65.3±6.4 years. The results of the histological examination for these noncancerous liver tissue samples indicate findings corresponding to chronic hepatitis four samples and findings corresponding to cirrhosis in eight samples.

As a validation cohort, normal liver tissue samples (C11 to C35) without noticeable histological findings were obtained from specimens surgically resected from 25 patients without HCC who were negative for both HBs-Ag and anti-HCV. These patients included 20 men and 5 women, and the average age was 61.8±7.1 years. Twenty-one of these patients underwent partial hepatectomy for liver metastases of primary colon cancer and the four remaining patients underwent partial hepatectomy for liver metastases of gastrointestinal stromal tumor in the stomach, stomach cancer, and colon carcinoid tumor, respectively.

Further, 22 samples (N13 to N34) of noncancerous liver tissue were obtained from 22 patients who underwent partial hepatectomy for HCC. These patients included 20 men and 2 women, and the average age was 61.9±8.5 years. Of these samples, 4 samples were positive for HBs-Ag, 16 samples were positive for anti-HCV, and 2 samples were negative for both. In addition, the results of the histological examination for these noncancerous liver tissue samples indicated findings corresponding to chronic hepatitis in 13 samples and findings corresponding to cirrhosis in 9 samples.

For comparison, primary HCC samples (T1 to T34) were also obtained from surgical specimens of the patients who provided the samples N1 to N34. For further comparison, 14 liver tissue samples (V1 to V14) were obtained from 14 patients without HCC development who were positive for HBs-Ag or anti-HCV. These patients included five men and eight women, and the average age was 65.1±8.2 years. Twelve of these patients underwent partial hepatectomy for liver metastases of primary colorectal cancer, and two patients underwent partial hepatectomy for liver metastases of stomach cancer.

The study using these human samples was approved by the Ethics Committee of the National Cancer Center in Japan and conducted with the informed consent of all the patients.

<DNA Extraction and DNA Bisulfite Modification>

High molecular weight DNA was extracted by phenol-chloroform from fresh frozen tissue samples which was obtained by chopping tissue just after sampling, followed by quick-frozen in liquid nitrogen, and preserving the tissue in liquid nitrogen. The extracted DNA was then subjected to dialysis. Bisulfite conversion was carried out using 1 μg of genomic DNA and the reagents of the EpiTect Bisulfite Kit (produced by QIAGEN GmbH) according to the manufacturer's protocol. It has been shown that this conversion process converts unmethylated cytosine residues into uracil, while methylated cytosine residues remain unconverted (see Clark S J et al., Nucleic Acids Res., 1994, volume 22, page 2990-7.)

<Pyrosequencing DNA Methylation Analysis>

The DNA methylation level (rate) was determined by an advanced quantitative procedure using pyrosequencing (registered trademark) technique. First, a polymerase chain reaction (PCR) primer (forward primer and reverse primer) and a sequencing primer were designed base on the bisulfite-converted sequence using Pyrosequencing Assay Design Software ver. 1.0 (produced by QIAGEN GmbH). In order to solve PCR bias in DNA methylation analysis, the annealing temperature was optimized as described in Shen L et al., Bio Techniques, 2007, volume 42, page 48-58, and Gao W et al., Carcinogenesis, 2008, volume 29, page 1901-10. Each of the primer sequences and the conditions of PCR are shown in Tables 1 and 2. The base sequences containing the CpG site, which were investigated by each PCR, are shown in Table 3.

TABLE 1

| Region | Number of CpG sites | Chromosome | Location of CpG site (NCBI Build 36.1) | BAC Clone | Base Sequence of Primer | | Conditions of PCR | |
|---|---|---|---|---|---|---|---|---|
| 1 | 1 | 1 | 31,052,829 | RP11-104J13 | Forward (SEQ ID NO: 1) | GTTGGGTGGGGTAGAATT | 54° C. 30 sec | x 50 cycles |
| | | | | | Reverse (SEQ ID NO: 2) | Biotin-AAACAAAACCTAACAAAATACC | 56° C. 30 sec | |
| | | | | | Sequencing (SEQ ID NO: 3) | GGATTAGGATTGTGGGATG | 72° C. 1 min | |
| 2 | 3 | 1 | 31,093,130 | RP11-104J13 | Forward (SEQ ID NO: 4) | GTAGTGATTTGGGTAGTAGGGAT | 94° C. 30 sec | x 50 cycles |
| | | | 31,093,140 | | Reverse (SEQ ID NO: 5) | Biotin-CTAATACTTCTCTCACCCACACA | 56° C. 30 sec | |
| | | | 31,093,145 | | Sequencing (SEQ ID NO: 6) | GAAATTTGTAGTTGGGGTAA | 72° C. 1 min | |
| 3 | 2 | 1 | 31,153,486 | RP11-104J13 | Forward (SEQ ID NO: 7) | AAAAGTGGTTATGGTTTGGGTATA | 94° C. 30 sec | x 5 cycles |
| | | | | | | | 94° C. 30 sec | x 5 cycles |
| | | | | | | | 94° C. 30 sec | x 5 cycles |
| | | | | | | | 94° C. 30 sec | x 35 cycles |
| | | | 31,153,497 | | Reverse (SEQ ID NO: 8) | Biotin-TATTCCCCCACCTCCCAATAA | 62° C. 30 sec | |
| | | | | | | | 62° C. 30 sec | |
| | | | | | | | 56° C. 30 sec | |
| | | | | | | | 56° C. 30 sec | |
| | | | | | Sequencing (SEQ ID NO: 9) | GTTTTTTAGGTTAGAGTAGG | 72° C. 1 min | |
| | | | | | | | 72° C. 1 min | |
| | | | | | | | 72° C. 1 min | |
| | | | | | | | 72° C. 1 min | |

TABLE 1-continued

| Region | Number of CpG sites | Chromo-some | Location of CpG site (NCBI Build 36.1) | BAC Clone | | Base Sequence of Primer | Conditions of PCR | |
|---|---|---|---|---|---|---|---|---|
| 4 | 1 | 1 | 31,175,443 | RP11-104J13 | Forward (SEQ ID NO: 10) | AGGGTTATTATATAAATTGAGGAATGTA | 54° C. 30 sec | × 50 cycles |
| | | | | | Reverse (SEQ ID NO: 11) | Biotin-ACATAAAAACAAACCCCTCCAT | 56° C. 30 sec | |
| | | | | | Sequencing (SEQ ID NO: 12) | TGTAGGTATTTAGTGTGTGA | | |
| 5 | 3 | 1 | 47,677,654 | RP11-52I2 | Forward (SEQ ID NO: 13) | AGGGTAGAGGTTTTTTTTTTTATAG | 94° C. 30 sec | × 50 cycles |
| | | | 47,677,660 | | Reverse (SEQ ID NO: 14) | Biotin-ATCAACATAACCAAAACCTAAACTTA | 54° C. 30 sec | |
| | | | 47,677,663 | | Sequencing (SEQ ID NO: 15) | TTTATACATTATATTATGGG | 72° C. 1 min | |
| 6 | 1 | 1 | 120,071,093 | RP11-29O22 | Forward (SEQ ID NO: 16) | GTTGTTATGGGTAGTGATTGTGTA | 94° C. 30 sec | × 50 cycles |
| | | | | | Reverse (SEQ ID NO: 17) | Biotin-TTCAACTCTATTCCCATAAACTACAA | 56° C. 30 sec | |
| | | | | | Sequencing (SEQ ID NO: 18) | TTATTTGGGTTTAGGG | 72° C. 1 min | |
| 7 | 1 | 2 | 235,289,886 | RP11-21K1 | Forward (SEQ ID NO: 19) | GTTTTTTAGGTGTTGGTTGATTAT | 94° C. 30 sec | × 50 cycles |
| | | | | | Reverse (SEQ ID NO: 20) | Biotin-AACCCAAACTAAATCACTCTAATAC | 56° C. 30 sec | |
| | | | | | Sequencing (SEQ ID NO: 21) | TAGGATTAGGAGTAGGAA | 72° C. 1 min | |
| 8 | 1 | 5 | 151,709,946 | RP11-169B16 | Forward (SEQ ID No: 22) | TATGAGGTTTAGAGAGGTTGTTATGT | 94° C. 30 sec | × 50 cycles |
| | | | | | Reverse (SEQ ID NO: 23) | Biotin-CTACTTTACCAATAAACAACCTACAT | 56° C. 30 sec | |
| | | | | | Sequencing (SEQ ID NO: 24) | TCGTTAGTAGGAAAGAAT | 72° C. 1 min | |
| 9 | 2 | 7 | 44,315,806 | RP11-112B7 | Forward (SEQ ID NO: 25) | TTAGGGGTTGTTTTGGATTATATTA | 94° C. 30 sec | × 5 cycles |
| | | | | | | | 94° C. 30 sec | × 5 cycles |
| | | | | | | | 94° C. 30 sec | × 5 cycles |
| | | | | | | | 94° C. 30 sec | × 35 cycles |
| | | | 44,315,810 | | Reverse (SEQ ID NO: 26) | Biotin-TTAAATCCACTCAAATCCCACTACT | 60° C. 30 sec | |
| | | | | | | | 56° C. 30 sec | |
| | | | | | | | 56° C. 30 sec | |
| | | | | | | | 54° C. 30 sec | |

TABLE 1-continued

| Region | Number of CpG sites | Chromo- some | Location of CpG site (NCBI Build 36.1) | BAC Clone | | Base Sequence of Primer | Conditions of PCR | |
|---|---|---|---|---|---|---|---|---|
| | | | | | Sequencing (SEQ ID NO: 27) | TTAGTTGTGGAAAGGATATA | 72° C. 1 min 72° C. 1 min 72° C. 1 min 72° C. 1 min | |
| 10 | 2 | 11 | 3,617,363 | RP11- 120E20 | Forward (SEQ ID NO: 28) | GTAGTAGATGGATTTTTTTGAGGA | 94° C. 30 sec | x 50 cycles |
| | | | | | Reverse (SEQ ID NO: 29) | Biotin- CCAAAATATCCTTACACAATAATCC | 56° C. 30 sec | |
| | | | | | Sequencing (SEQ ID NO: 30) | ATTTTTTTTTTAATTAAGTG | 72° C. 1 min | |
| 11 | 2 | 11 | 3,724,633 3,724,650 | RF11- 120E20 | Forward (SEQ ID NO: 31) | GGTAGATTATTTGAGGTTAGGAGTT | 94° C. 30 sec | x 50 cycles |
| | | | | | Reverse (SEQ ID NO: 32) | Biotin- CAAATCATTTTATAATAATCCCTTTAC | 54° C. 30 sec | |
| | | | | | Sequencing (SEQ ID NO: 33) | AAGGTTGAAGTAGGAGAAT | 72° C. 1 min | |
| 12 | 1 | 11 | 118,716,221 | RP11- 334E6 | Forward (SEQ ID NO: 34) | TGGTTAGGAGTGTTTGGAAG | 94° C. 30 sec 94° C. 30 sec 94° C. 30 sec 94° C. 30 sec | x 5 cycles x 5 cycles x 5 cycles x 35 cycles |
| | | | | | Reverse (SEQ ID NO: 35) | Biotin- ATCCTACCTAATCCACAAACTAC | 56° C. 30 sec 56° C. 30 sec 54° C. 30 sec 52° C. 30 sec | |
| | | | | | Sequencing (SEQ ID NO: 36) | GGAGTGTTTGGAAGG | 72° C. 1 min 72° C. 1 min 72° C. 1 min 72° C. 1 min | |
| 13 | 1 | 11 | 118,798,005 | RP11- 334E6 | Forward (SEQ ID NO: 37) | GTAGGGTATTGTTTAGGTTGAGTG | 94° C. 30 sec | x 50 cycles |
| | | | | | Reverse (SEQ ID NO: 38) | Biotin- CCTTCCTCCTAAATCTAACTCAAA | 54° C. 30 sec | |
| | | | | | Sequencing (SEQ ID NO: 39) | GGTATTGTTTAGGTTGAGTG | 72° C. 1 min | |
| 14 | 4 | 11 | 132,094,250 | RP11- 17I7 | Forward (SEQ ID NO: 40) | TTATAGAAGGGAAGGGAGTTTTGTAA | 94° C. 30 sec 94° C. 30 sec 94° C. 30 sec 94° C. 30 sec | x 5 cycles x 5 cycles x 5 cycles x 35 cycles |

TABLE 1-continued

| Region | Number of CpG sites | Chromo- some | Location of CpG site (NCBI Build 36.1) | BAC Clone | | Base Sequence of Primer | Conditions of PCR | |
|---|---|---|---|---|---|---|---|---|
| | | | 132,094,254 | | Reverse (SEQ ID NO: 41) | Biotin- CCACTCACAAAACATAACCTATTTCTC | 60° C. 30 sec 57° C. 30 sec 54° C. 30 sec 51° C. 30 sec | |
| | | | 132,094,256 132,094,259 | | Sequencing (SEQ ID NO: 42) | TAGGTATTGGTTTTTTGG | 72° C. 1 min 72° C. 1 min 72° C. 1 min 72° C. 1 min | |
| 15 | 1 | 11 | 132,143,897 | RP11- 17217 | Forward (SEQ ID NO: 43) | TTGAGTGTTAGTTACGTTTTTAGTAAG | 94° C. 30 sec 94° C. 30 sec 94° C. 30 sec 94° C. 30 sec | x 5 cycles x 5 cycles x 5 cycles x 35 cycles |
| | | | | | Reverse (SEQ ID NO: 44) | Biotin- CAAATAAAATACTCCTTTCATCTATATC | 60° C. 30 sec 57° C. 30 sec 54° C. 50 sec 51° C. 30 sec | |
| | | | | | Sequencing (SEQ ID NO: 45) | GGTTTTTAGTAAGGAGAT | 72° C. 1 min 72° C. 1 min 72° C. 1 min 72° C. 1 min | |

TABLE 2

| Region | Number of CpG sites | Chromo- some | Location of CpG site NCBI Build 36.1 | BAC Clone | | Base Sequence of Primer | Conditions of PCR | |
|---|---|---|---|---|---|---|---|---|
| 16 | 1 | 11 | 132,186,602 | RP11- 17X17 | Forward (SEQ ID NO: 46) | TATTGAATTATAGGTGTAGAAGGGAGTTA | 94° C. 30 sec 94° C. 30 sec 94° C. 30 sec 94° C. 30 sec | x 5 cycles x 5 cycles x5 cycles x35 cycles |
| | | | | | Reverse (SEQ ID NO: 47) | Biotin- ATCTTTAAACCAAAACAACCACTTTC | 59° C. 30 sec 58° C. 30 sec 58° C. 30 sec 58° C. 30 sec | |

TABLE 2-continued

| Region | Number of CpG sites | Chromosome | Location of CpG site NCBI Build 36.1) | BAC Clone | | Base Sequence of Primer | | Conditions of PCR | |
|---|---|---|---|---|---|---|---|---|---|
| | | | | | Sequencing (SEQ ID NO: 48) | TAGAAGAGTTTGATTAGG | 72° C. 1 min 72° C. 1 min 72° C. 1 min 72° C. 1 min | |
| 17 | 1 | 11 | 5,190,237 | RP11-319E16 | Forward (SEQ ID NO: 49) | GGGAGGGTTTGTAGTTAAGGTAT | 94° C. 30 sec | × 50 cycles |
| | | | | | Reverse (SEQ ID NO: 50) | Biotin-ACAAATAACACCCCATCTCCTA | 56° C. 30 sec | |
| | | | | | Sequencing (SEQ ID NO: 51) | GGGAGGGTTTGTAGTTAAG | 72° C. 1 min | |
| 18 | 2 | 12 | 5,239,770 | RP11-391E16 | Forward (SEQ ID NO: 52) | AGAAGAAAGAAATTTTTTAATGGAGAATAT | 94° C. 30 sec | × 50 cycles |
| | | | 5,239,778 | | Reverse (SEQ ID NO: 53) | Biotin-CTTTCCCTACCACCTTATATCTACCTATTT | 54° C. 30 sec | |
| | | | | | Sequencing (SEQ ID NO: 54) | GTTTTTTTTATTTATAGATG | 72° C. 1 min | |
| 19 | 1 | 12 | 50,601,217 | RP11-1200L3 | Forward (SEQ ID NO: 55) | AGTTAAAAATATAGTTGGGTTGAAAT | 94°C. 30 sec | × 50 cycles |
| | | | | | Reverse (SEQ ID NO: 56) | Biotin-AATTCCCTAACTTAACACTCTAACT | 54° C. 30 sec | |
| | | | | | Sequencing (SEQ ID NO: 57) | TTTTATGGTTAGTATGGTG | 72° C. 1 min | |
| 20 | 2 | 12 | 50,687,010 | RP11-1100L3 | Forward (SEQ ID NO: 58) | GGAGTTTATAAAGGGAGG | 94° C. 30 sec | × 50 cycles |
| | | | 50,687,013 | | Reverse (SEQ ID NO: 59) | Biotin-TCCTTCTACTACAACTTCCTAAAT | 54° C. 30 sec | |
| | | | | | Sequencing (SEQ ID NO: 60) | AGTTAGGTTGGTATTTTTTA | 72° C. 1 min | |
| 21 | 1 | 12 | 55,681,393 | RP11-79906 | Forward (SEQ ID NO: 61) | AAGGTTTTGTGAGTTAATGAAA | 94° C. 30 sec | × 50 cycles |
| | | | | | Reverse (SEQ ID NO: 62) | Biotin-CACCCTACTCAAATAAACTCTAAA | 54° C. 30 sec | |
| | | | | | Sequencing (SEQ ID NO: 63) | TTATTTGTTTGTGAAATAG | 72° C. 1 min | |
| 22 | 2 | 12 | 55,732,381 | RP11-79906 | Forward (SEQ ID NO: 64) | GGGTGTTTGTAATTTTAGTTATTTAGGA | 94° C. 30 sec | × 50 cycles |
| | | | 55,732,391 | | Reverse (SEQ ID NO: 65) | Biotin-CCCAATTTATCAAAAATCAACACCA | 54° C. 30 sec | |
| | | | | | Sequencing (SEQ ID NO: 66) | GGAGATTAAGGTAGGAGAA | 72° C. 1 min | |

TABLE 2-continued

| Region | Number of CpG sites | Chromosome | Location of CpG site NCBI Build 36.1) | BAC Clone | | Base Sequence of Primer | Conditions of PCR | |
|---|---|---|---|---|---|---|---|---|
| 23 | 1 | 16 | 4,538,435 | RP11-89W4 | Forward (SEQ ID NO: 67) | AGATTTTATTATAATTGGGGTAGTA | 94° C. 30 sec | x 50 cycles |
| | | | | | Reverse (SEQ ID NO: 68) | Biotin-AAAAACCCCATAAACTAACTCT | 56° C. 30 sec | |
| | | | | | Sequencing (SEQ ID NO: 69) | AGGAGTGTTGTAGGTT | 72° C. 1 min | |
| 24 | 1 | 16 | 4,564,846 | RP11-89W4 | Forward (SEQ ID NO: 70) | AGAATTGGAAGATGGTTGTATTGT | 94° C. 30 sec | x 50 cycles |
| | | | | | Reverse (SEQ ID NO: 71) | Biotin-CCAAACTATATTCTCCTCCTTACA | 56° C. 30 sec | |
| | | | | | Sequencing (SEQ ID NO: 72) | TTTTTGGGATTTTTTAAT | 72° C. 1 min | |
| 25 | 1 | 16 | 4,642,726 | RP11-89M4 | Forward (SEQ ID NO: 73) | TATTGGAGAAGAGGGTTGTGTTTATAT | 94° C. 1 min | x 5 cycles |
| | | | | | | | 94° C. 1 min | x 5 cycles |
| | | | | | | | 94° C. 1 min | x 5 cycles |
| | | | | | | | 94° C. 1 min | x 35 cycles |
| | | | | | Reverse (SEQ ID NO: 74) | Biotin-CCCCCAAACTCACACTACCCTAC | 54° C. 1 min | |
| | | | | | | | 62° C. 1 min | |
| | | | | | | | 50° C. 1 min | |
| | | | | | | | 58° C. 1 min | |
| | | | | | Sequencing (SEQ ID NO: 75) | GAGGATGGTGATAAGT | 72° C. 1 min | |
| | | | | | | | 72° C. 1 min | |
| | | | | | | | 72° C. 1 min | |
| | | | | | | | 72° C. 1 min | |
| 26 | 1 | 16 | 4,655,181 | RP11-89M4 | Forward (SEQ ID NO: 76) | AGTAGTGGTGGAAGTGATTGGT | 94° C. 1 min | x 5 cycles |
| | | | | | | | 94° C. 1 min | x 5 cycles |
| | | | | | | | 94° C. 1 min | x 5 cycles |
| | | | | | | | 94° C. 1 min | x 35 cycles |
| | | | | | Reverse (SEQ ID NO: 77) | Biotin-CCCAACCCCTACTCAAACTTCT | 64° C. 1 min | |
| | | | | | | | 62° C. 1 min | |
| | | | | | | | 60° C. 1 min | |
| | | | | | | | 59° C. 1 min | |
| | | | | | Sequencing (SEQ ID NO: 78) | AAGTGTTATTTGGTTATTAT | 72° C. 1 min | |
| | | | | | | | 72° C. 1 min | |
| | | | | | | | 72° C. 1 min | |
| | | | | | | | 72° C. 1 min | |

TABLE 2-continued

| Region | Number of CpG sites | Chromosome | Location of CpG site NCBI Build 36.1) | BAC Clone | | Base Sequence of Primer | Conditions of PCR | |
|---|---|---|---|---|---|---|---|---|
| 27 | 1 | 16 | 4,672,961 | RP11-89M4 | Forward (SEQ ID NO: 79) | AGTTGGTTTTGAGGGAAAGTAGT | 94° C. 1 min | x 50 cycles |
| | | | | | Reverse (SEQ ID NO: 80) | Biotin-CTCCACCAAAAAATACTACCTCC | 56° C. 1 min | |
| | | | | | Sequencing (SEQ ID NO: 81) | GGTTTTGAGGGAAAGTAG | 72° C. 1 min | |
| 28 | 2 | 19 | 4,999,458 | RP11-346B12 | Forward (SEQ ID NO: 82) | TAGGTTTTATAGTTAGGAGGGTAGG | 94° C. 1 min | x 50 cycles |
| | | | 4,999,468 | | Reverse (SEQ ID NO: 83) | Biotin-CCCAAACACCCAACAAATTC | 56° C. 1 min | |
| | | | | | Sequencing (SEQ ID NO: 84) | TTTTATAGTTAGGAGGGTA | 72° C. 1 min | |
| 29 | 1 | 19 | 4,998,744 | RP11-348B12 | Forward (SEQ ID NO: 85) | AGTTTAAGTTTTGGTGAGTGTTTG | 94° C. 1 min | x 50 cycles |
| | | | | | Reverse (SEQ ID NO: 86) | Biotin-TCACCTAATAAAACCCCTACCAC | 59° C. 1 min | |
| | | | | | Sequencing (SEQ ID NO: 87) | GGGAGGGAGTTAATTT | 72° C. 1 min | |
| 30 | 2 | 19 | 5,099,166 | RP11-348B12 | Forward (SEQ ID NO: 88) | TTGGGGTGGGTTTAGGTGATA | 94° C. 1 min | x 50 cycles |
| | | | 5,099,171 | | Reverse (SEQ ID NO: 89) | Biotin-TTCCTCCCAATAACCTCCCTAAA | 56° C. 1 min | |
| | | | | | Sequencing (SEQ ID NO: 90) | GGGTAAGAAGTTATTATAGG | 72° C. 1 min | |

TABLE 3

| Region | Sequence | SEQ ID NO: |
|---|---|---|
| 1 | T G T G G G A T G C T T C C C A C C C C G C C C C<br>C G C C C C G G G C C G C C G C C C G C C G C C C | 91 |
| 2 | G G G C A A C C T T C C C T G C G T C A T C T C C<br>C G G G G C G G G C G G C C C T G T G T G G G | 92 |
| 3 | G T C C T T C T C G C G C C T C C C A G G C C A G<br>C G C A G G G G T C C C G C T T C G T C C C C G G | 93 |
| 4 | A C T C T G G A A G A G A G A C C A A G A A T G C<br>C G G T A C C C A G T G T G T G A C G A C A G C C | 94 |
| 5 | T A G A C C A C A T C A T G G G C C A C G G T G G<br>C G G C G G G G C A G C A C C C C C G G G C G C C | 95 |
| 6 | A C T C G C C C C A C C T G G G C T C A G G G C C<br>C G G G G T C C A C T C A T G T T G C T G A C T T | 96 |
| 7 | A G C A C A G G G A T C A G G A G C A G G A A G C C<br>C G G G G T C T C C C A T T T C A G A G A G C A G | 97 |
| 8 | A C A C T G G T T A G C A G G A A A G A A C A C C<br>C G G G T T T G T G T G C G C A C C G G T C T A T | 98 |

TABLE 3-continued

| Region | Sequence | SEQ ID NO: |
|---|---|---|
| 9 | AGCTGTGGAAAGGACACAGCCTCCT CGCCCCGGGCAGGAGCGCCCGCGGGG | 99 |
| 10 | TTCCCCTTTAACCAAGTGGGTCTCC CGAAGGCCCCGGGGATTATTGTGTA | 100 |
| 11 | CTCGGGAAGGCTGAAGCAGGAGAAT CGCTTGAGCCCGGGAGGCGGAGGTT | 101 |
| 12 | TGGTGGCCCGGCGTGCCTGGAAGGC CGGGGTGCCCCGGGCAGAGGCTGGG | 102 |
| 13 | CGCGAGAGCGCGCAGGGCATTGCCT CGGTTGAGTGCGCCCGGGTGCGCAG | 103 |
| 14 | ACAGGCACTGGCTCTCTGGCCCGGG CGCGCCGTCCAGGAGGCGCGTGTTC | 104 |
| 15 | CAGCCAGGCCCCCAGCAAGGAGACC CGGGCTCCCCAGGTGAAGTTCCTTA | 105 |
| 16 | TTTCTAGAAGAGCCTGATTAGGCCC CGGGAAAGTGGCTGTTTTGGTTTAA | 106 |
| 17 | TTGCAGCCAAGGCATTTATGCCCCC CGGGGCTCCCTTCTGTCATCCCTCC | 107 |
| 18 | CCCTTCTCATTTACAGATGAAGAAT CGGAGGCCCGGGTAGGGGAGGAGAC | 108 |
| 19 | AGCATGGTGCACCCCCTACCACTCC CGGGACAGGATGCAAAAGAGGCTCC | 109 |
| 20 | GCCCGCCCGGCTGGCATCCCCCAGC CGCCGCCAGCCCCGCCGAGGGGAGC | 110 |
| 21 | AAAACCACTTGCTTGTGAAACAGCC CGGGGTGTTGCTGAATCCCACCAGG | 111 |
| 22 | ACTCAGGAGACTAAGGCAGGAGAAT CGCTTGAACCCGGGTGGTGGAGGTT | 112 |
| 23 | TGGGGCAGCAGGAGTGCTGTAGGCC CGGGACATCTTCAGTGACAGGTGTC | 113 |
| 24 | CTCCCCTGGGACCCCCCAACCTCC CGGGTCCTGGGTGCTGAGGGTAGGG | 114 |
| 25 | CCCCACCGAGGACGGCGACAAGCCC CGGGTGCTCTACAGCCTGGAGTTCA | 115 |
| 26 | AAGTGCCATCTGGCCATCACTTTCC CGGGGACCTGGGAGCTGGGCAGGGG | 116 |
| 27 | CAGCTCCCCTGAGGTGAGGCCCCCC CGGGGAAGCTTTGCGCACCCGCCCG | 117 |
| 28 | CTGCCCTGCACTGTCCTCCAAGGGC CGCTAGGTGGCGCTCCCGCCCTTCC | 118 |
| 29 | GAGCCCCTCGGGAGGGAGTCAATCC CGGGTACACGGCTGGGCGCCGTGGC | 119 |
| 30 | AGACGTCACCACAGGGAGCCCGGGC CGAGGCGCACGCCTCTGATTTCCTG | 120 |

Underlined "CG" in sequences indicates CpG sites described in Table 1 and 2.

The PCR was carried out with 7.5 ng of bisulfite-treated DNA and 0.6 units of AmpliTaq Gold (produced by Applied Biosystems). Since the PCR products were obtained by amplification using biotin-labeled reverse primers as shown in Tables 1 and 2, the PCR products were purified with streptoavidin-coated beads (Streptavidin Sepharose (registered trademark) High Performance, produced by GE Healthcare).

Subsequently, quantitative sequencing was carried out on PyroMark Q24 (produced by QIAGEN) using the Pyro Gold reagents (produced by QIAGEN) according to the manufacturer's protocol. For each assay, Epitect methylated human control DNA (produced by QIAGEN) was used as a positive control, and Epitect unmethylated human control DNA (produced by QIAGEN) was used as a negative control. The PCR products were confirmed to be specific products having an appropriate size by fraction on electrophoresis with 3% agarose gel and staining with ethidium bromide, and confirmed to be free of nonspecific products by amplification. FIG. 1 shows representative pyrograms obtained by pyrosequencing DNA methylation analysis. The DNA methylation level (%) in each CpG site, as also shown in FIG. 1, was calculated by the following formula.

DNA Methylation Level (%)=Luminescence Intensity of Cytosine×100/(Luminescence Intensity of Cytosine+Luminescence Intensity of Thymine)

<Statistics>

The significant differences in DNA methylation level at each of the CpG sites between sample groups were analyzed by the Mann-Whitney U test. The survival curves of the group of patients with HCC were calculated by the Kaplan-Meier method, and their differences were compared by the log-rank test and determined to be significant when $p<0.05$.

Example 1

<Validation of BAMCA Data by Pyrosequencing>

Figure 2:
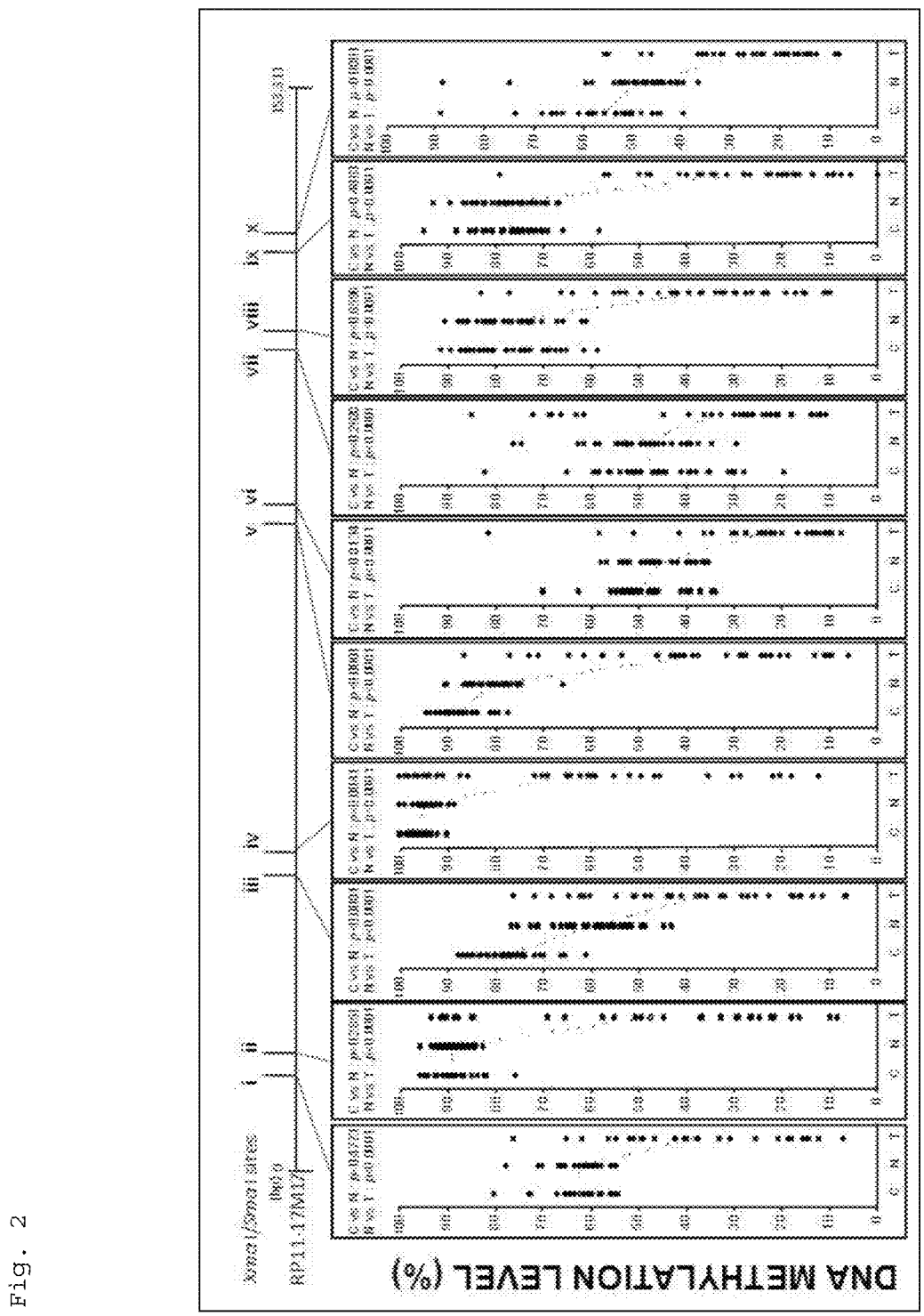
FIG. 2 shows schematic diagrams and scatter diagrams of BAC clones, which are examples of results obtained by verifying again with pyrosequencing the analysis results obtained by BAMCA. In the schematic diagrams of the BAC clone in the figure, i to X indicate respective locations of 10 XmaI/SmaI sites that yield PCR products of 2000 bp or less to be effectively assessed by BAMCA, on a RP11-17M 17 BAC clone. The scatter diagrams show results of assessment of the DNA methylation levels at the 10 XmaI/SmaI sites by pyrosequencing. "C" indicates results of normal liver tissue samples (C11 to C35), "N" indicates results of 22 noncancerous liver tissue samples (N13 to N34), and "T" indicates results of primary HCC samples (T1 to T34) obtained from specimens surgically removed from the patients who provide the samples N1 to N34.

BAMCA can provide an overview of DNA methylation tendency of respective large regions in all chromosomes (see NPLs 13 and 19). The present inventors have identified, by BAMCA, 25 BAC clones whose DNA methylation status can distinguish between normal liver tissues obtained from patients without HCC and noncancerous liver tissues obtained from patients with HCC in a learning cohort (see NPL 18). For example, as shown in FIG. 2, 10 XmaI/SmaI sites on RP11-17M17 were effectively assessed by BAMCA. The previous study results of the present inventors have showed that the average signal ratio of these BAC clones by BAMCA is significantly lower in noncancerous liver tissue samples obtained from patients with HCC than in normal liver tissue samples and is significantly lower in HCC than in noncancerous liver tissue samples obtained from patients with HCC.

The DNA methylation levels at all XmaI/SmaI restriction enzyme recognition sites, which yielded PCR products of 2000 bp or less to be effectively assessed by BAMCA, were quantitatively assessed again using pyrosequencing. The obtained results, i.e., the average DNA methylation levels determined by pyrosequencing for 10 XmaI/SmaI sites on the RP11-17M 17 BAC clone in 34 noncancerous liver tissue samples obtained from patients with HCC are shown in FIGS. 2 and 3.

Figure 3:
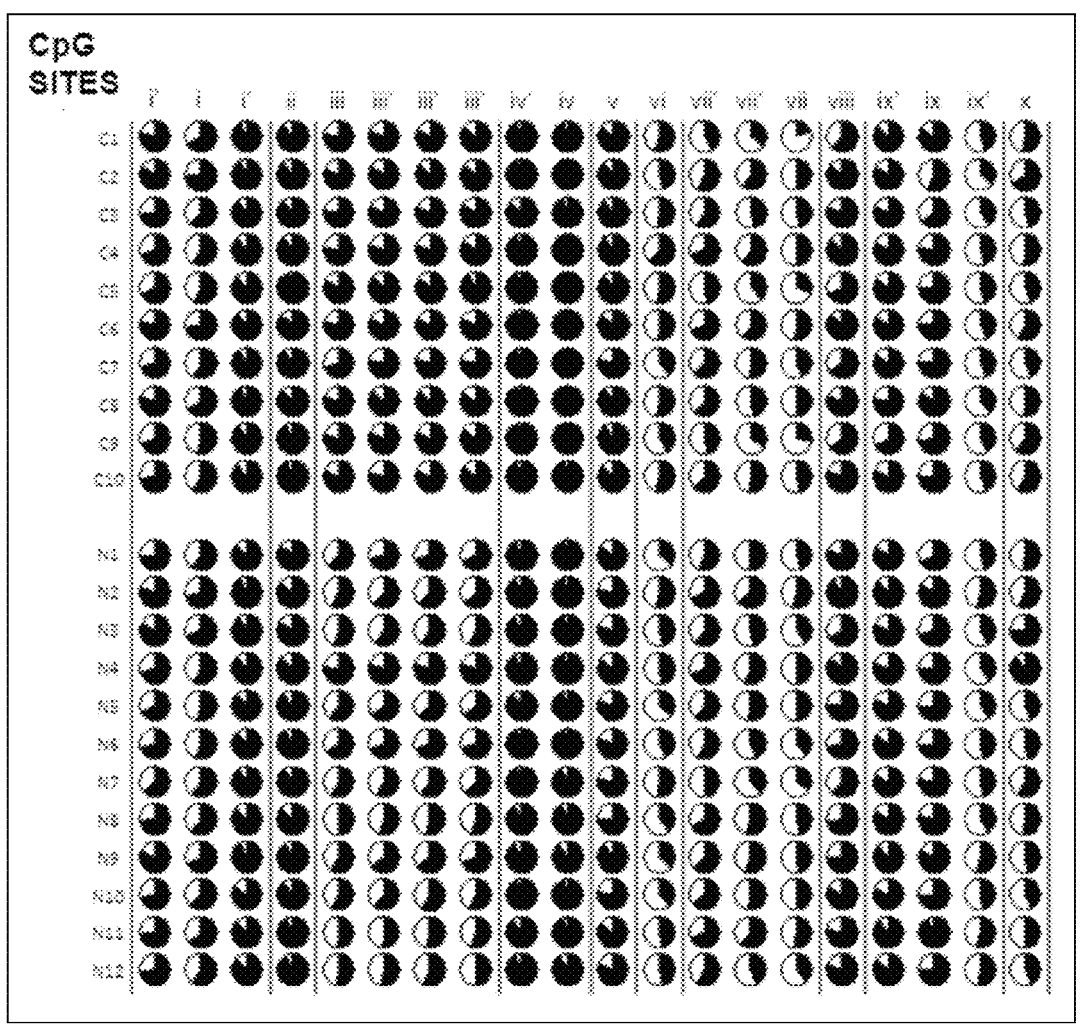
FIG. 3 shows pie charts of DNA methylation level at each CpG site in Samples C(C1 to C10) and Samples N (N1 to C12). In the figure, i', iii', iv', vii', and ix' indicate CpG sites near XmaI/SmaI sites (i, iii, iv, vii, and ix) which are quantitatively sequenced using the same sequencing primer, respectively. In the pie charts, black indicates the ratio of methylated cytosine and white indicates the ratio of unmethylated cytosine.

The results in FIGS. 2 and 3 showed that the average DNA methylation levels of XmaI/SmaI sites, i, ii, vii, viii, and ix, in 34 noncancerous liver tissue samples, which were determined by pyrosequencing, were the same as those in normal liver tissue samples. The average DNA methylation level of XmaI/SmaI sites, iii, iv, v, vi, and x, in 34 noncancerous liver tissue samples was significantly lower than that in 35 normal liver tissue samples. Moreover, the DNA methylation levels of XmaI/SmaI sites, i to x, in 34 HCC (hepatocellular carcinoma) samples were significantly lower than those in noncancerous liver tissue samples obtained from patients with HCC (see FIG. 2).

Furthermore, for example, in the CpG sites, iii, iv, and iv', the DNA methylation levels of the CpG sites near the XmaI/SmaI sites, which were quantitatively sequenced using the same sequencing primer, were found to have a tendency close to those at the XmaI/SmaI sites themselves for each sample (see FIG. 3). Accordingly, it was confirmed that BAMCA was able to detect alternation of DNA methylation which cooperatively occurred on RP11-17M17.

In another BAC clone RP11-799O6 which was also identified as an indicator for cancer risk assessment in the previous study results of the present inventors, the average signal ratio obtained by BAMCA was shown to be significantly higher in the noncancerous liver tissue samples from patients with HCC than in the normal liver tissue samples (see NPL 18). As with RP11-17M17, the average DNA methylation level of ten XmaI/SmaI sites, which yielded PCR products of 2000 bp or less to be effectively assessed by BAMCA, was analyzed by pyrosequencing. As a result, although not shown in the figure, the average DNA methylation level of seven XmaI/SmaI sites in the noncancerous liver tissue samples obtained from patients with HCC was the same as that in the normal liver tissue samples. The average DNA methylation level of three XmaI/SmaI sites in the noncancerous liver tissue samples obtained from the patients with HCC was significantly higher than that in the normal liver tissue samples.

Accordingly, the data on the BAC clones which were identified as indicators for cancer risk estimation by BAMCA were evaluated again for validity by pyrosequencing.

Example 2

<Establishment of Criteria for Cancer Risk Assessment Using Liver Tissue Samples Based on Pyrosequencing>

In order to identify the CpG sites which were most effective for diagnosis and to improve the sensitivity and specificity in assessment of cancer risk, based on the criteria identified from the previous analysis results of the present inventors by BAMCA (see NPL 18), the DNA methylation levels at 203 CpG sites on 25 BAC clones were measured by pyrosequencing using primer sets encompassing the XmaI/SmaI sites, which were assessed as effective by BAMCA, on the 25 BAC clones.

As a result of the measurement, the Mann-Whitney U test ($p<0.001$) revealed that the average DNA methylation levels at 59 CpG sites were significantly different between normal liver tissues and noncancerous liver tissues obtained from patients with HCC in the learning cohort.

In order to establish the criteria with high reproducibility, 14 CpG sites which have an average DNA methylation level of 10% or less in normal liver tissues and noncancerous liver tissues obtained from patients with HCC were excluded from candidates of the criteria for cancer risk estimation in consideration of characteristics of the pyrosequencing technology (see Shen L et al., Bio Techniques, 2007, volume 42, page 48-58.) When several CpG sites may be measured using one sequencing primer, one cutoff value was set for one region covered by the sequencing primer using the average DNA methylation levels of the several CpG sites. As representative examples of the obtained results, the scatter diagrams of the normal liver tissue samples and the noncancerous liver tissue samples obtained from the patients with HCC are shown in FIG. 4.

Figure 4:
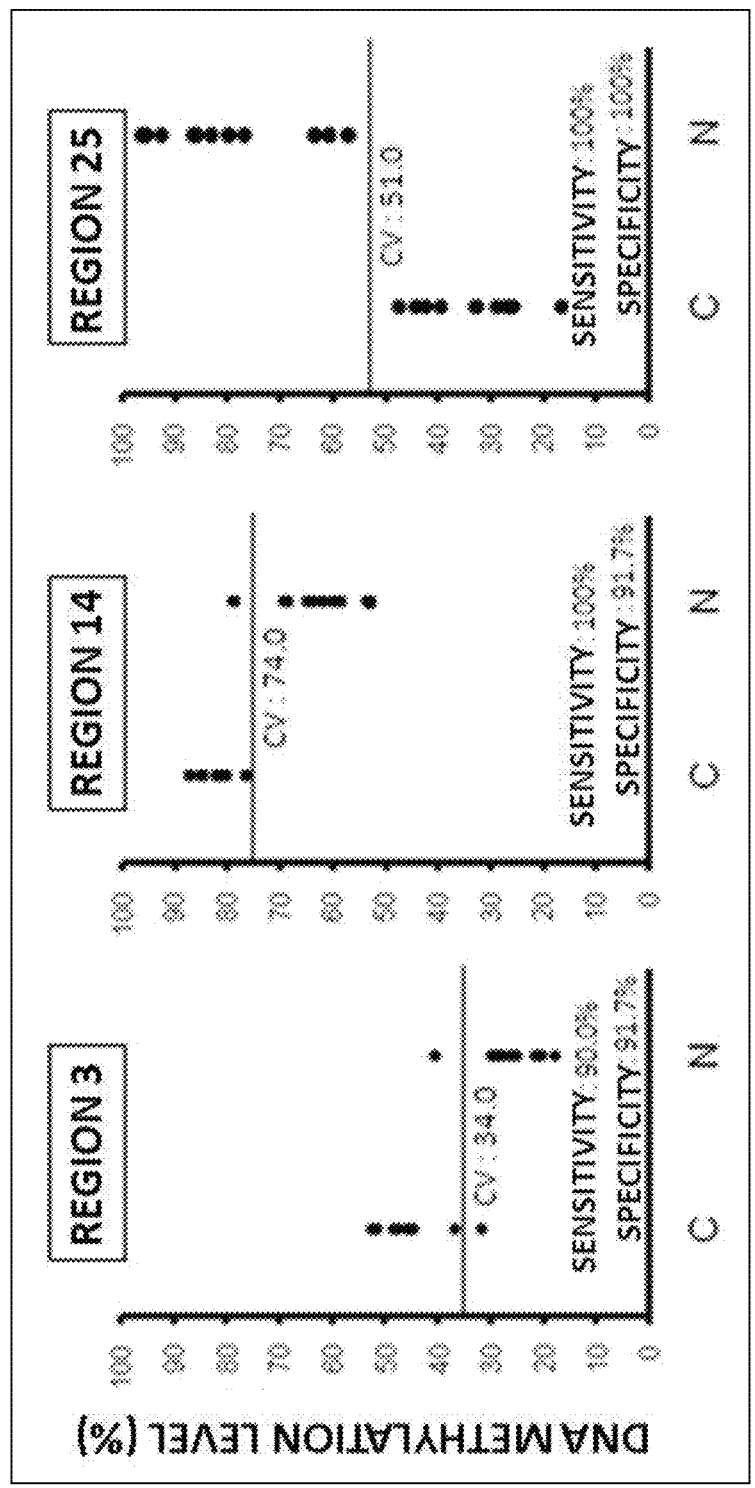
FIG. 4 shows scatter diagrams of representative results for DNA methylation levels analyzed by pyrosequencing. In the figure, "C" indicates results of normal liver tissue samples (C1 to C10), "N" indicates results of 22 noncancerous liver tissue samples (N1 to N12), and "Region 3", "Region 14", and "Region 25" correspond to the regions shown in Table 4, respectively. Furthermore, "CV" indicates the cutoff value to distinguish between Samples N and Samples C based on the DNA methylation level of each region.

The results in FIG. 4 showed that for each region, the cutoff values were set which were able to distinguish between the noncancerous liver tissues obtained from the patients with HCC and the normal liver tissues in the learning cohort with sufficient sensitivity and specificity. At the remaining 45 CpG sites including the regions shown in FIG. 4, the cutoff values were set similarly which were able to distinguish between them with a sensitivity and specificity of 70% or more.

In this way, 30 cutoff values (criteria) were set for 30 regions containing 45 CpG sites. The sensitivity and specificity in each region are shown in Table 4. The chromosomal loci and characteristics of the 30 regions (whether a CpG island or not, whether an exon or intron of a specific gene or noncoding region) are also summarized in Table 4.

tissue samples were analyzed by pyrosequencing as a validation study. The obtained results are shown in FIG. 6.

Figure 6:
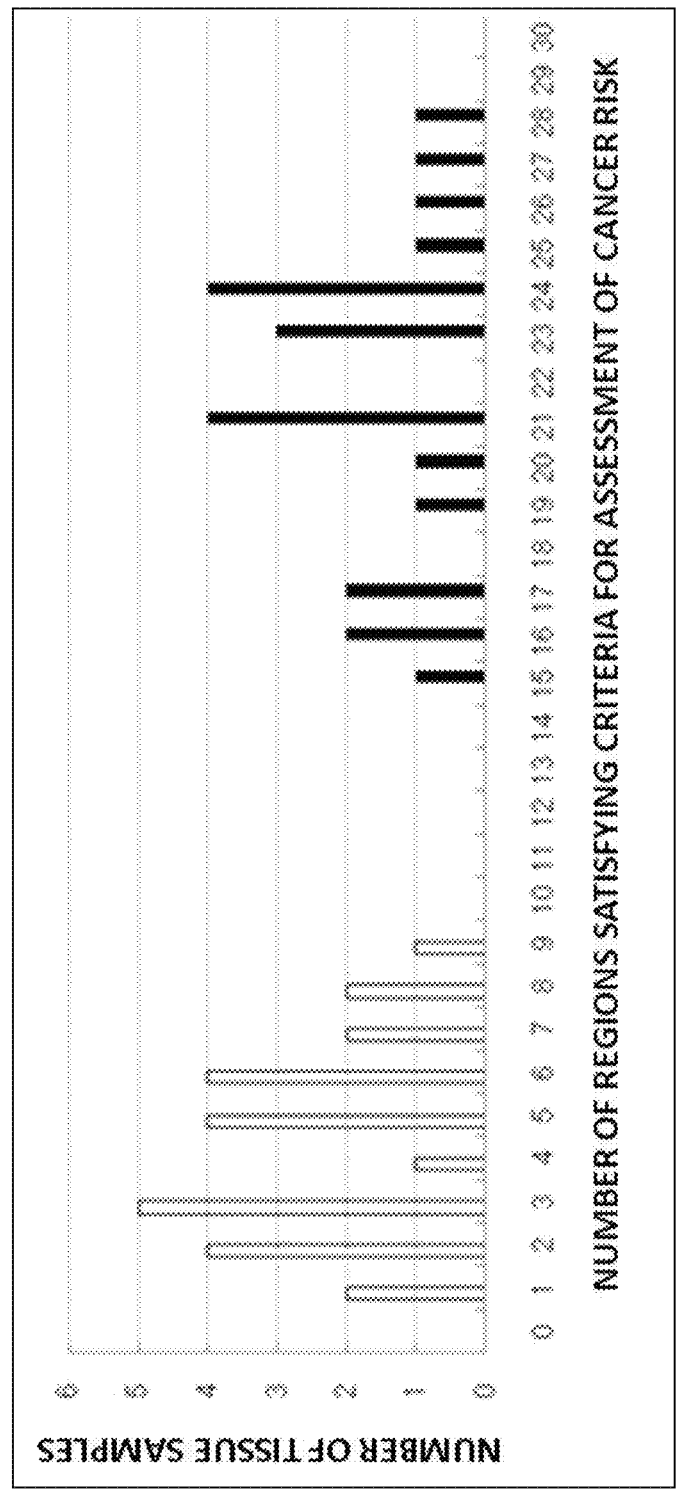
FIG. 6 shows a histogram of the relationship of Samples C (C11 to C35) and Samples N (N13 to N34) with the number of regions satisfying the criteria (criteria shown in Table 4) for assessment of cancer risk in each sample. In the figure, white columns indicate Samples C and black columns indicates Samples N.

The results in FIG. 6 showed that all 22 samples for validation which satisfied the criteria described in Table 4 for 15 or more regions were the noncancerous liver tissues (N13 to N34) obtained from the patients with HCC. It is also confirmed that all 25 samples for validation which did not satisfied the criteria described in Table 4 for 15 or more regions were the normal liver tissues (C11 to C35).

Accordingly, it was found that these criteria allow the noncancerous liver tissues obtained from the patients with HCC in the validation cohort to be diagnosed as high cancer risk with a sensitivity and specificity both of 100%.

Example 3

<Cancer Risk Assessment Using Samples of Liver Tissues Based on Pyrosequencing in Extended Validation Cohort>

In order to confirm the reliability of the criteria for cancer risk estimation established in Example 2, the cancer risk was

TABLE 4

Thirty regions that were able to distinguish between noncancerous liver tissues (N) from hepatocellular carcinoma cases and normal liver tissues (C)

| Region | BAC clone ID | Chromosomal location | Characteristics | Gene | Cutoff value (%) | DNA methylation status* | Sensitivity (%) | Specificity (%) |
|---|---|---|---|---|---|---|---|---|
| 1 | RP11-104J13 | 1p35.2 | Noncoding/CpG island | None | 25.5 | C > N | 80.0 | 66.7 |
| 2 | RP11-104J13 | 1p35.2 | Noncoding | None | 26.0 | C > N | 90.0 | 91.7 |
| 3 | RP11-104J13 | 1p35.2 | First intron/CpG island | SDC3 | 34.0 | C > N | 90.0 | 91.7 |
| 4 | RP11-104J13 | 1p35.2 | Noncoding | None | 88.9 | C < N | 100 | 66.7 |
| 5 | RP11-52I2 | 1p33 | First exon/CpG island | POXD2 | 47.5 | C > N | 90.0 | 91.7 |
| 6 | RP11-29M22 | 1p12 | Intron | PHODE | 73.0 | C < N | 100 | 50.0 |
| 7 | RP11-21K1 | 2p37.1 | Noncoding | None | 93.0 | C > N | 80.0 | 50.0 |
| 8 | RP11-109B15 | 5p33.1 | Noncoding | None | 12.0 | C > N | 60.0 | 83.3 |
| 9 | RP11-112B7 | 7p13 | First intron/CpG island | CAMK25 | 45.0 | C > N | 20.0 | 91.7 |
| 10 | RP11-120E20 | 11p15.4 | Intron | ART5 | 85.2 | C > N | 50.0 | 100 |
| 11 | RP11-120E20 | 11p15.4 | Intron/SINE repeat | NUP98 | 95.7 | C < N | 100 | 75.0 |
| 12 | RP11-334E6 | 11q23.3 | First exon/CpG island | C1QTNF5 | 23.7 | C < N | 100 | 25.0 |
| 13 | RP11-334E6 | 11q23.3 | First intron/CpG island | THY1 | 12.6 | C > N | 60.0 | 83.3 |
| 14 | RP11-17M17 | 11q25 | First intron | OPCML | 74.0 | C > N | 100 | 91.7 |
| 15 | RP11-17N17 | 11q25 | First intron | OPCML | 79.0 | C > N | 100 | 33.3 |
| 16 | RP11-17M17 | 11q25 | First intron | OPCML | 49.7 | C > N | 70.0 | 50.0 |
| 17 | RP11-319E16 | 12P13.32 | Noncoding | None | 79.0 | C > N | 70.0 | 58.3 |
| 18 | RP11-319E16 | 12p13.32 | Noncoding/SINE repeat | None | 45.0 | C > N | 100 | 50.0 |
| 19 | RP11-1100L3 | 12q13.13 | UTR | ACVRL1 | 50.0 | C < N | 90.0 | 63.3 |
| 20 | RP11-1100L3 | 12q13.13 | Promoter/CpG island | GRASP | 7.0 | C > N | 80.0 | 58.3 |
| 21 | RP11-799O6 | 12q13.3 | UTR | ZETB39 | 40.0 | C < N | 100 | 91.7 |
| 22 | RP11-799O6 | 12q13.3 | Noncoding/SINE repeat | None | 89.0 | C < N | 80.0 | 100 |
| 23 | RP11-89M4 | 16p13.3 | Noncoding | None | 38.0 | C < N | 70.0 | 100 |
| 24 | RP11-89M4 | 16p13.3 | Intron | LOC342346 | 69.0 | C > N | 100 | 33.3 |
| 25 | RP11-89M4 | 16p13.3 | Exon/CpG island | MGRN1 | 51.0 | C < N | 100 | 100 |
| 26 | RP11-89M4 | 16p13.3 | Intron | MGRN1 | 28.0 | C < N | 100 | 50.0 |
| 27 | RP11-89M4 | 16p13.3 | Intron/CpG island | MGRN1 | 67.0 | C < N | 100 | 100 |
| 28 | RP11-348B12 | 19p13.3 | Intron/CpG island | KDN4B | 44.0 | C < N | 100 | 100 |
| 29 | RP11-348B12 | 19p13.3 | Intron/CpG island | KDM4B | 94.8 | C < N | 100 | 41.7 |
| 30 | RP11-348B12 | 19p13.3 | Intron/CpG island | KDN4B | 94.0 | C > N | 50.0 | 91.7 |

*C > N: When the DNA methylation level (rete) is lower than the cut off value, the tissue analyte is determined to be in a group of high carcinogenic risk.
*C < N: When the DNA methylation level (rate) is higher than the cut off value, the tissue analyte is determined to be in a group of high carcinogenic risk.

Figure 5:
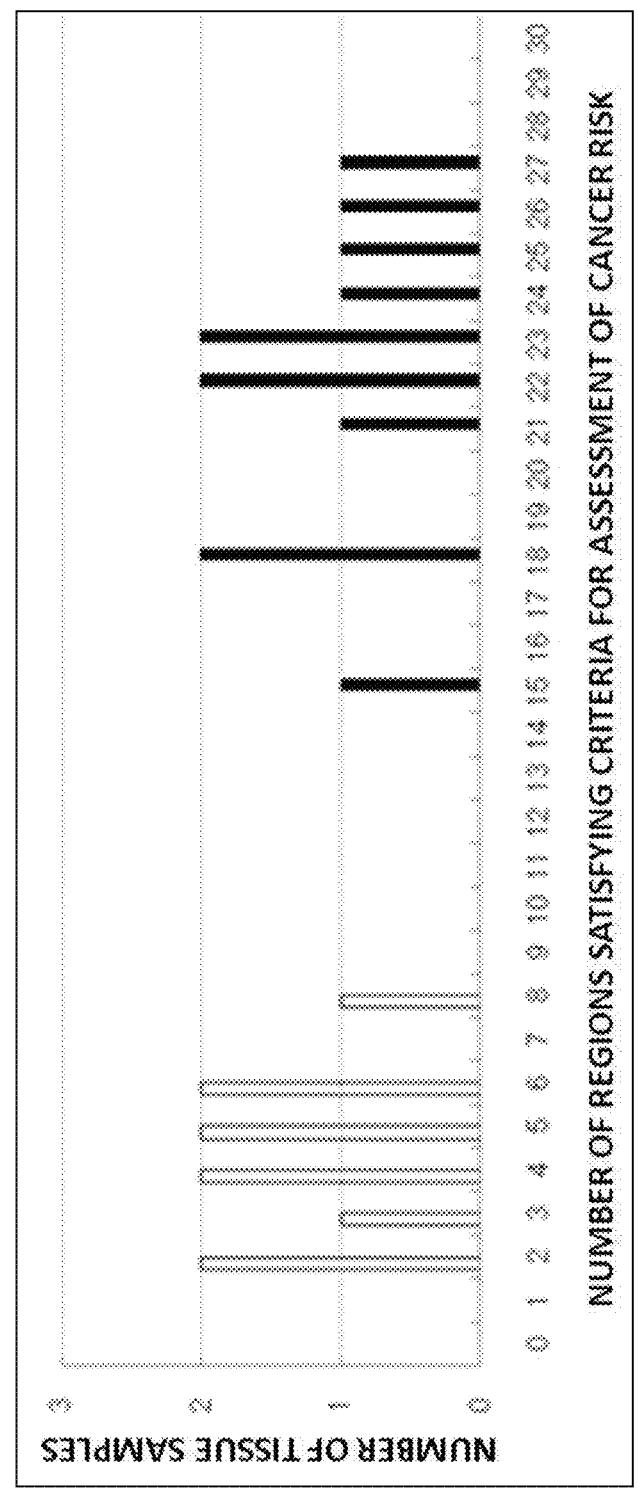
FIG. 5 shows a histogram of the relationship of Samples C (C1 to C10) and Samples N (N1 to N12) with the number of regions satisfying the criteria (criteria shown in Table 4) for assessment of cancer risk in each sample. In the figure, white columns indicate Samples C and black columns indicates Samples N.

A histogram indicating the number of regions satisfying the criteria described in Table 4 for the Samples C1 to C10 and N1 to N12 in the learning cohort is shown in FIG. 5.

The results in FIG. 5 showed that when the liver tissue satisfying the criteria described in Table 4 for 15 or more regions was determined as high cancer risk, the noncancerous liver tissue obtained from the patients with HCC was able to be distinguished from the normal liver tissue with a sensitivity and specificity of 100% in the learning cohort. Then, in order to confirm these criteria, 47 additional liver assessed using the criteria in more cases (extended validation cohort) than those in Example 2.

Specifically, normal liver tissue samples (C11 to C35, C44 to C63) without noticeable histological findings were first obtained from specimens surgically resected from 45 patients without HCC who were negative for both HBs-Ag and anti-HCV. These patients included 34 men and 11 women, and the average age was 62.2±7.0 years. Of these patients, patients underwent partial hepatectomy for liver metastases of primary colon cancer, 3 patients underwent partial hepatectomy for liver metastases of stomach cancer, and 3 remaining patients underwent partial hepatectomy for liver metastases of gastrointestinal stromal tumor in the stomach, pancreatic cancer, and colon carcinoid tumor, respectively. Further, 45 samples (N13 to N34, N47 to N69) of noncancerous liver tissues were obtained from 45 patients who underwent partial hepatectomy for HCC. These patients included 37 men and 8 women, and the average age was 62.3±9.7 years. Of these samples, 13 samples were positive for HBs-Ag, 29 samples were positive for anti-HCV, and 13 samples were negative for both. In addition, the results of the histological examination for these noncancerous liver tissue samples indicated findings corresponding to chronic hepatitis in 22 samples and findings corresponding to cirrhosis in 23 samples. The study using these human samples was approved by the Ethics Committee of the National Cancer Center in Japan and conducted with the informed consent of all the patients.

These tissue samples were subjected to pyrosequencing with the primers and conditions shown in Tables 1 to 3 according to the methods described in the sections of <DNA Extraction and DNA Bisulfite Modification> and <Pyrosequencing DNA Methylation Analysis>. The obtained results are shown in FIG. 7.

Figure 7:
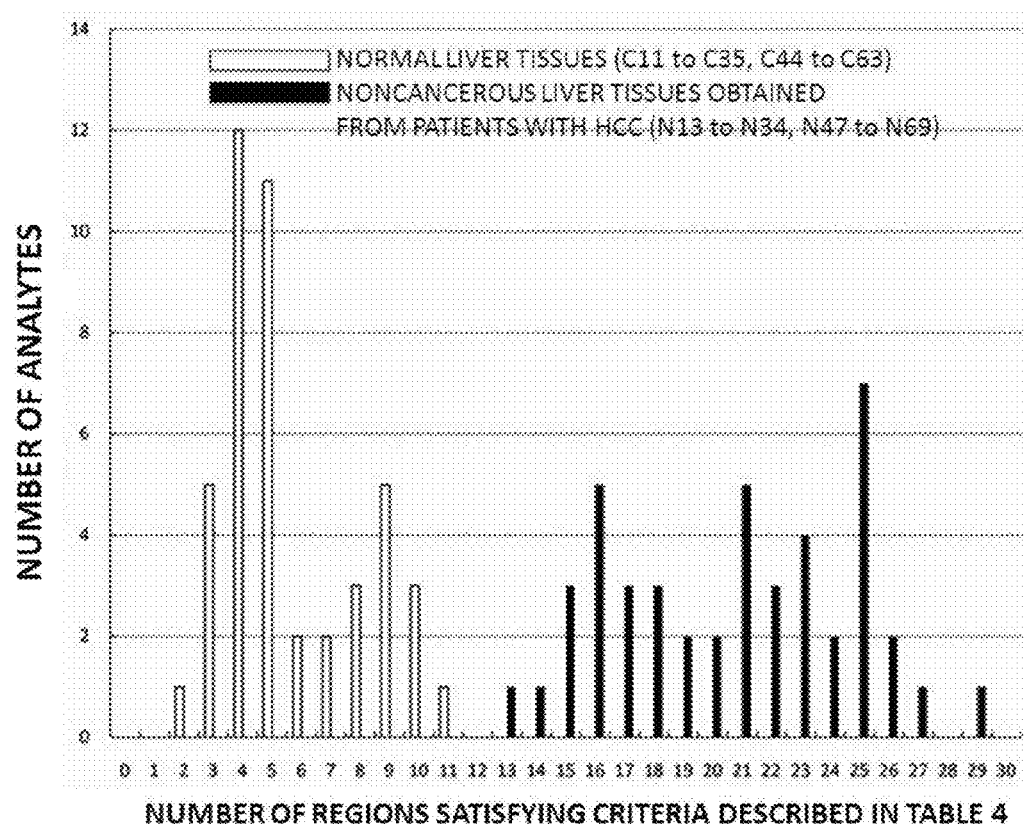
FIG. 7 shows a histogram of the relationship of Samples C (C11 to C35, C44 to C63) and Samples N (N13 to N34, N47 to N69) with the number of regions satisfying the criteria (criteria shown in Table 4) for assessment of cancer risk in each sample. In the figure, white columns indicate Samples C and black columns indicates Samples N.

The results in FIG. 7 showed that all 45 samples for validation which satisfied the criteria described in Table 4 for 13 or more regions were the noncancerous liver tissues (N13 to N34, N47 to N69) obtained from the patients with HCC. It is also confirmed that all 45 samples for validation which did not satisfy the criteria described in Table 4 for 13 or more regions were the normal liver tissues (C11 to C35, C44 to C63).

Accordingly, the extended validation cohort also revealed that the DNA methylation status was different in the noncancerous liver tissues obtained from the patients with HCC and the normal liver tissues, and the noncancerous liver tissues obtained from the patients with HCC were able to be diagnosed as high cancer risk based on the DNA methylation status.

Example 4

<Clinicopathological Significance of DNA Methylation Status in 30 Regions Described in Table 4>

In order to evaluate clinicopathological significance of the DNA methylation status in 30 regions described in Table 4, 34 noncancerous liver tissue samples (N1 to N34) from patients with HCC in the learning cohort and the validation cohort were divided into two groups according to the number of regions satisfying the criteria. Specifically, 34 noncancerous liver tissue samples from patients with HCC were divided into a group with 23 or more regions satisfying the criteria and a group with less than 23 regions satisfying the criteria on the basis of the median (i.e., 23) of the number of regions satisfying the criteria described in Table 4. The prognosis of these patients was followed up for 11 to 3936 days (average: 1417 days). The obtained results are shown in FIGS. 8 and 9.

Figure 8:
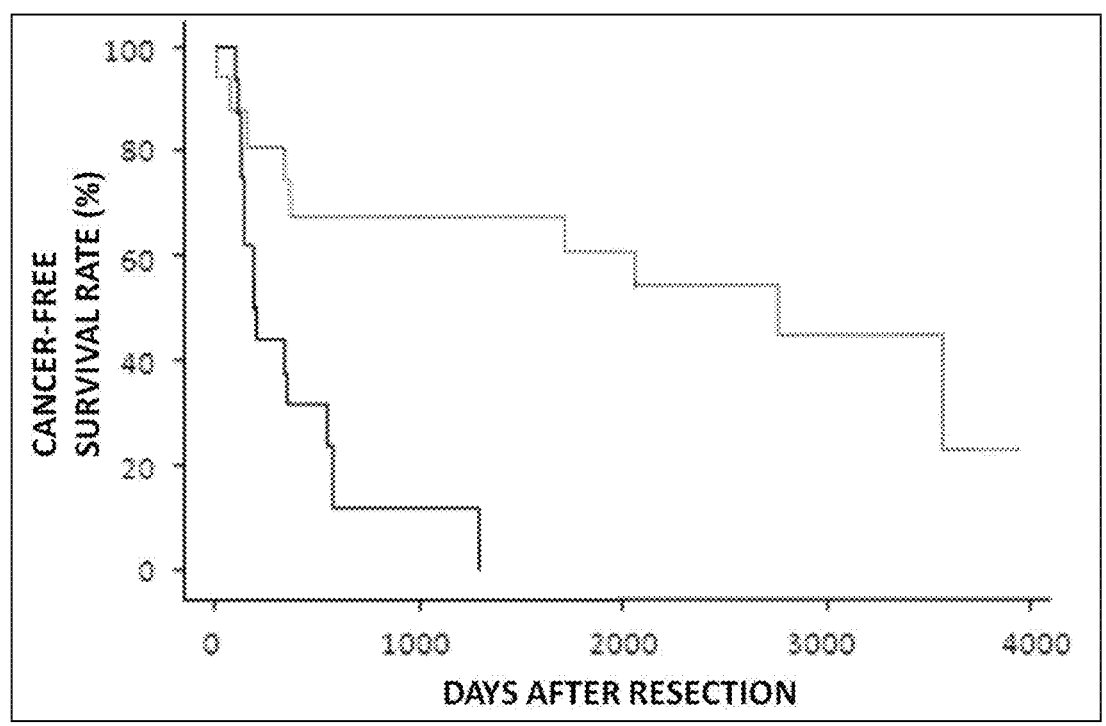
FIG. 8 shows graphs of the correlation between the DNA methylation status in a precancerous state and the prognosis (cancer-free survival rate) of patients with HCC, in which the survival curve of the group of patients with HCC (N1 to N34) is obtained by the Kaplan-Meier method. In the figure, solid lines indicate the patients with HCC (n=17) having 23 or more regions that satisfy the criteria shown in Table 4, and dotted lines indicate the patients with HCC (n=17) having less than 23 regions that satisfy the criteria shown in Table 4. The horizontal axis represents the days after liver resection in the patients with HCC.
Figure 9:
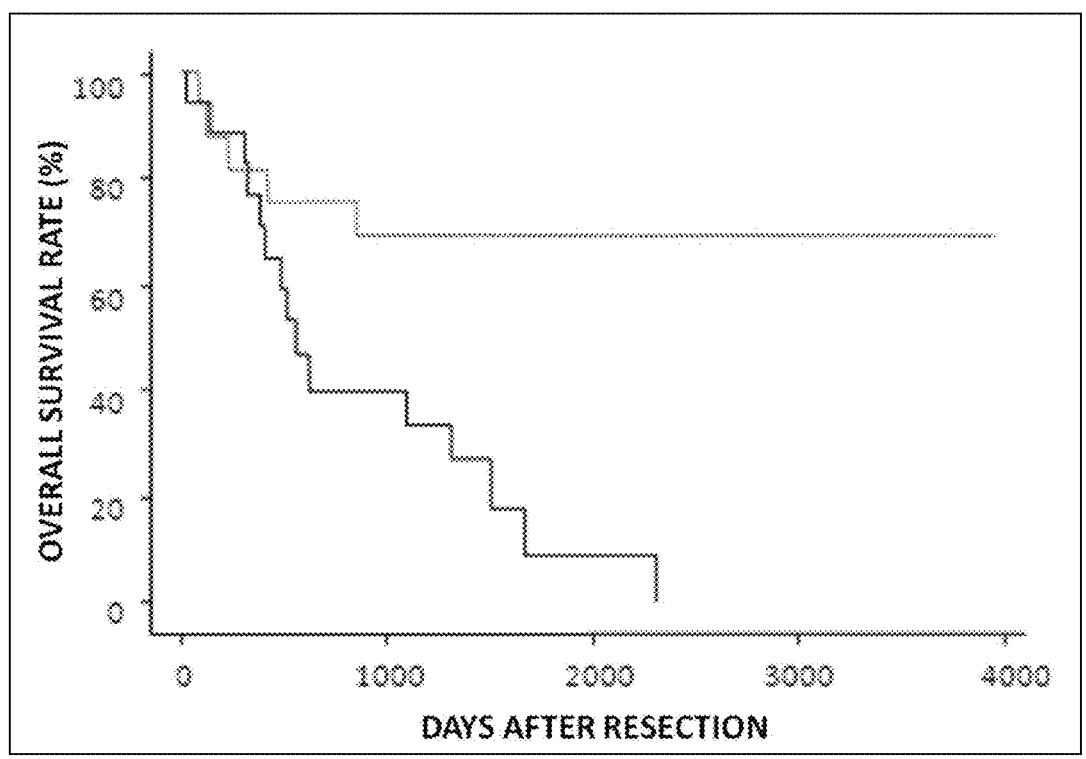
FIG. 9 shows graphs of the correlation between the DNA methylation status in a precancerous state and the prognosis (overall survival rate) of patients with HCC, in which the survival curve of the group of patients with HCC(N1 to N34) is obtained by the Kaplan-Meier method. In the figure, solid lines indicate the patients with HCC (n=17) having 23 or more regions that satisfy the criteria shown in Table 4, and dotted lines indicate the patients with HCC (n=17) having less than 23 regions that satisfy the criteria shown in Table 4. The horizontal axis represents the days after liver resection in the patients with HCC.

The results in FIG. 8 and FIG. 9 showed that the cancer-free survival rate and the overall survival rate of the patients with HCC satisfying the criteria described in Table 4 for 23 or more regions in these noncancerous liver tissues were significantly lower than those of the patients with HCC satisfying the criteria for less than 23 regions (see FIG. 8 for cancer-free survival rate (p=0.0023), see FIG. 9 for overall survival rate (p=0.0015)).

Accordingly, these data showed that alteration of the DNA methylation having clinicopathological significance correlated with the prognosis of the patients was already established in a precancerous state.

It is also found that with respect to the noncancerous liver tissue samples (N1 to N34), the number of regions satisfying the criteria described in Table 4 is not significantly different between in the liver tissues with chronic hepatitis (n=17, 20.6±3.1) and in the liver tissues with cirrhosis (n=17, 22.9±3.8) (p=0.0525).

For further comparison, the DNA methylation levels of 30 regions in 14 additional liver tissue samples obtained from patients who were infected with HBV or HCV but without HCC development were analyzed by pyrosequencing. As a result, it was confirmed that the average number of regions satisfying the criteria described in Table 4 (12.0±5.0) was significantly lower in V1 to V14 than in N1 to N34 (21.7±3.6) (p<0.0001).

Accordingly, these data showed that the criteria did not simply reflect hepatitis virus infection, inflammation, or fibrosis at the stage of chronic hepatitis and cirrhosis, but in fact reflected cancer risk itself.

Example 5

<Validation 1 for Application of Criteria According to the Present Invention to Clinical Diagnosis>

For patients infected with HBV or HCV, during the surveillance (follow-up) period, the microscopic examination (histopathology) of liver biopsy specimens was carried out prior to interferon therapy in order to clarify baseline liver histology. If the cancer risk can be assessed based on the criteria using liver biopsy specimens sampled during the surveillance period, it is expected that the liver biopsy specimens can be effectively utilize and the burden on patients can be reduced.

In such histopathology, however, the tissues sampled for biopsy are usually fixed in formalin and embedded in paraffin. The reactions in PCR and pyrosequencing may be inhibited because DNA in the tissue is sheared. That is, when the tissues fixed in formalin or so are analyzed by pyrosequencing or the like, the regions susceptible to such reaction inhibition and less susceptible regions may be present in a base sequence-specific manner.

Accordingly, when the method of the present invention is carried out for the liver biopsy specimens sampled during the surveillance period, it can be expected that more reproducible results are obtained using only the regions less susceptible to the reaction inhibition than using all 30 regions described in Table 4 in order to assess cancer risk well.

Figure 10:
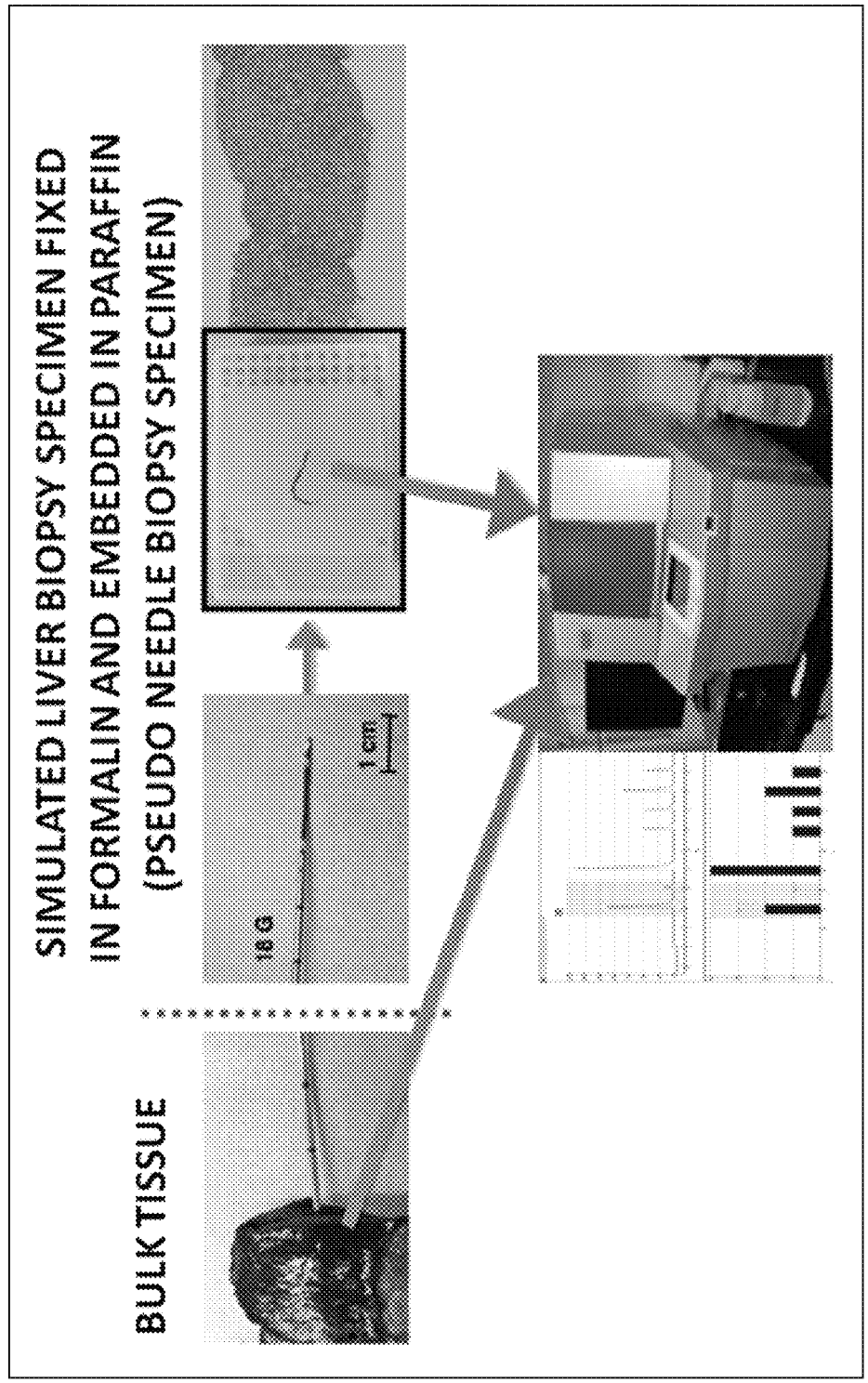
FIG. 10 shows an outline of DNA methylation analysis by pyrosequencing for a simulated specimen of liver biopsy sampled during the surveillance period (simulated liver biopsy specimen (pseudo needle biopsy specimen) sampled from a partial hepatectomy specimen).

The tissues after fixed in formalin and embedded in paraffin according to Tissue Sample and Method (see FIG. 10) described below were subjected to PCR and pyrosequencing, and it was attempted to identify, from 30 regions described in Table 4, the regions less susceptible to the reaction inhibition and suitable for carrying out the present invention for liver biopsy specimens.

<Tissue Sample and Method>

As simulated specimens of liver biopsy sampled during the surveillance period (simulated liver biopsy specimens sampled from partial hepatectomy specimens (pseudo needle biopsy specimens)), bulk tissues were pierced with an 18G needle to remove pieces of tissue with about 1 cm long and the obtained pieces of tissue were fixed in formalin and embedded in paraffin for preparation. Specifically, the obtained pieces of tissue were fixed in 10% formalin at room temperature for a day and night and dehydrated in 100% ethanol, which was further replaced by chloroform. Subsequently, they were sufficiently impregnated with paraffin and paraffin blocks were then produced.

As the bulk tissues, 19 normal liver tissue samples (C36 to C43, and C64 to C72) and 14 noncancerous liver tissue samples (N35 to N46, N70 and N71) were used. These samples are described below in detail.

The pseudo needle biopsy specimens of the normal liver tissue samples (C36 to C43) without noticeable histological findings were obtained from specimens surgically resected from 8 patients who suffered from other diseases than HCC and were negative for both HBs-Ag and anti-HCV. These patients included five men and three women, and the average age was 62.6±2.6 years. Seven of these patients underwent partial hepatectomy for liver metastases of primary colorectal cancer, and one patient underwent partial hepatectomy for liver metastases of gastrointestinal stromal tumor in the stomach.

Furthermore, the pseudo needle biopsy specimens of the normal liver tissue samples (C64 to C74) without noticeable histological findings were obtained from specimens surgically resected from 11 patients who suffered from other diseases than HCC and were negative for both HBs-Ag and anti-HCV. These patients included eight men and three women, and the average age was 57.5±10.7 years. Ten of these patients underwent partial hepatectomy for liver metastases of primary colorectal cancer, and one patient underwent partial hepatectomy for liver metastases of germ cell tumor in the testis.

The pseudo needle biopsy specimens of 12 samples (N35 to N46) of noncancerous liver tissues were obtained from specimens surgically resected from 12 patients who underwent partial hepatectomy for HCC. These patients included 10 men and 2 women, and the average age was 61.3±12.2 years. The results of the histological examination for these noncancerous liver tissue samples indicated findings corresponding to chronic hepatitis in four samples and findings corresponding to cirrhosis in five samples.

The pseudo needle biopsy specimens of two samples (N70 and N71) of noncancerous liver tissues were obtained from specimens surgically resected from two patients who underwent partial hepatectomy for HCC. These patients included one man and one woman, and the age was 73 and 63 years, respectively. The results of the histological examination for these noncancerous liver tissue samples indicated findings corresponding to chronic hepatitis in both two samples.

About 10 slices of specimens, which were 5-μm thick, were cut from the paraffin blocks of the pseudo needle biopsy specimens prepared as described above, and DNA was extracted using the reagents of QIAamp DNA FFPE Tissue Kit (produced by QIAGEN GmbH Co.) according to the manufacturer's protocol. Further, bisulfite modification was performed according to the method described in the section of <DNA Extraction and DNA Bisulfite Modification>.

Subsequently, these bisulfite modified samples were analyzed by the method described in the section of <Pyrosequencing DNA Methylation Analysis>. As a result, from 30 regions described in Table 4, 15 regions (Regions: 1 to 5, 14, 16, 18, 19, 21, 23, 25 to 28 described in Table 4) were identified as regions less susceptible to the reaction inhibition and suitable for carrying out the present invention for liver biopsy specimens.

Figure 11:
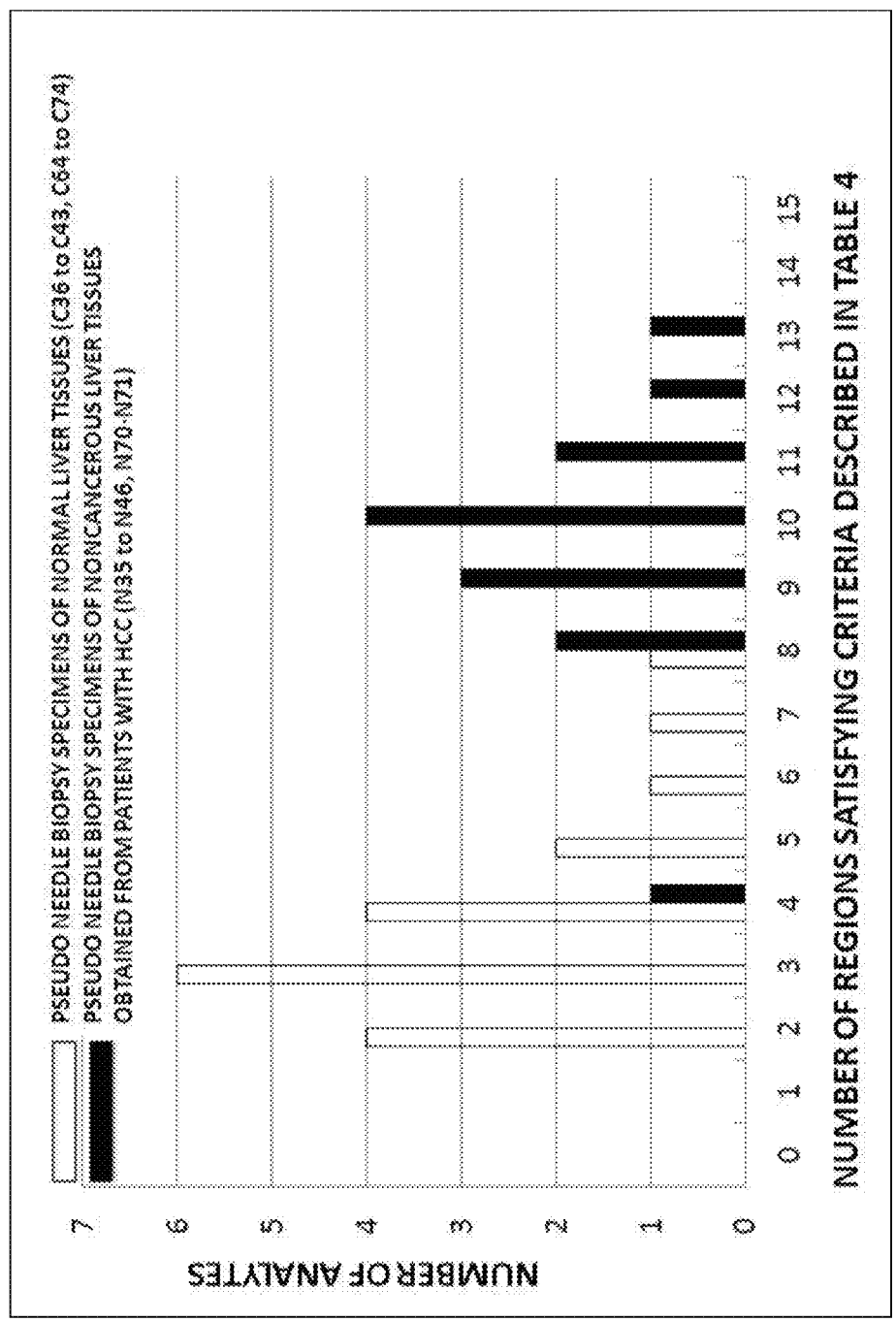
FIG. 11 shows a histogram of the relationship of the pseudo needle biopsy specimens (C36 to C43, and C64 to C74) from normal liver tissues and the pseudo needle biopsy specimens (N35 to N46, N70, and N71) from noncancerous liver tissues with the number of regions satisfying the criteria (criteria described in Table 4) for assessment of cancer risk for each pseudo needle biopsy specimen among 15 regions (Regions 1 to 5, 14, 16, 18, 19, 21, 23, 25 to 28) described in Table 4. In the figure, white columns indicate Samples C and black columns indicates Samples N.

FIG. 11 showed that when the liver tissues satisfying the criteria described in Table 4 for eight or more regions among these 15 regions were determined as high cancer risk, the pseudo needle biopsy specimens of noncancerous liver tissues were able to be distinguished from normal liver tissues with a sensitivity of 93% and a specificity of 95%.

Example 6

<Validation 2 for Application of Criteria According to the Present Invention to Clinical Diagnosis>

In clinical practice, liver biopsy specimens are usually sampled from the parts which are easily accessed from the body surface or the like and safely taken, and are not always sampled from near lesions of hepatocellular carcinoma. If the present invention can be carried out independent of the distance from lesions of hepatocellular carcinoma, the feasibility of the cancer risk diagnosis for liver biopsy specimens which have limitation in sampling site increases.

According to the same method as described in Example 5, tissues were sampled from more than one part of partial hepatectomy specimens to prepare pseudo needle biopsy specimens which were fixed in formalin and embedded in paraffin. Tissues were taken from more than one part of the partial hepatectomy specimens to prepare fresh frozen bulk tissues according to the method described in the section of <DNA Extraction and DNA Bisulfite Modification>. Subsequently, these pseudo needle biopsy specimens and fresh frozen bulk tissues were subjected to DNA extraction, bisulfite modification, and pyrosequencing DNA methylation analysis according to the above method to investigate the relationship between the distance from lesions of hepatocellular carcinoma and the DNA methylation status. A part of the obtained results (results in Regions 2 and 4 described in Table 4) is shown in FIGS. 12 and 13.

Figure 12:
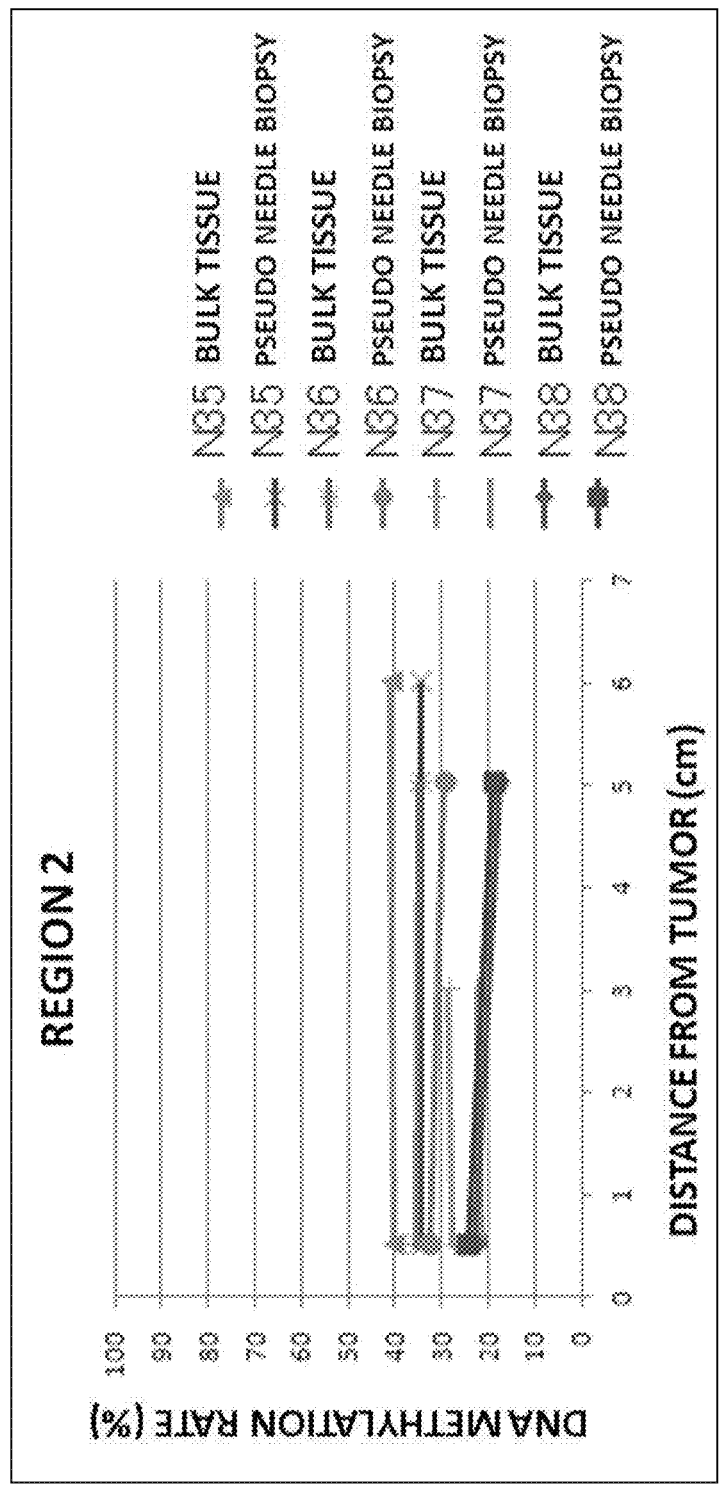
FIG. 12 shows a graph of the relationship between the DNA methylation level (rate) of Region 2 described in Table 4 and the distance from tumors (lesions of hepatocellular carcinoma) of sampled noncancerous liver tissues in noncancerous liver tissues (pseudo needle biopsy specimens or bulk tissues) sampled from the patients with HCC (N35 to N38) and prepared.
Figure 13:
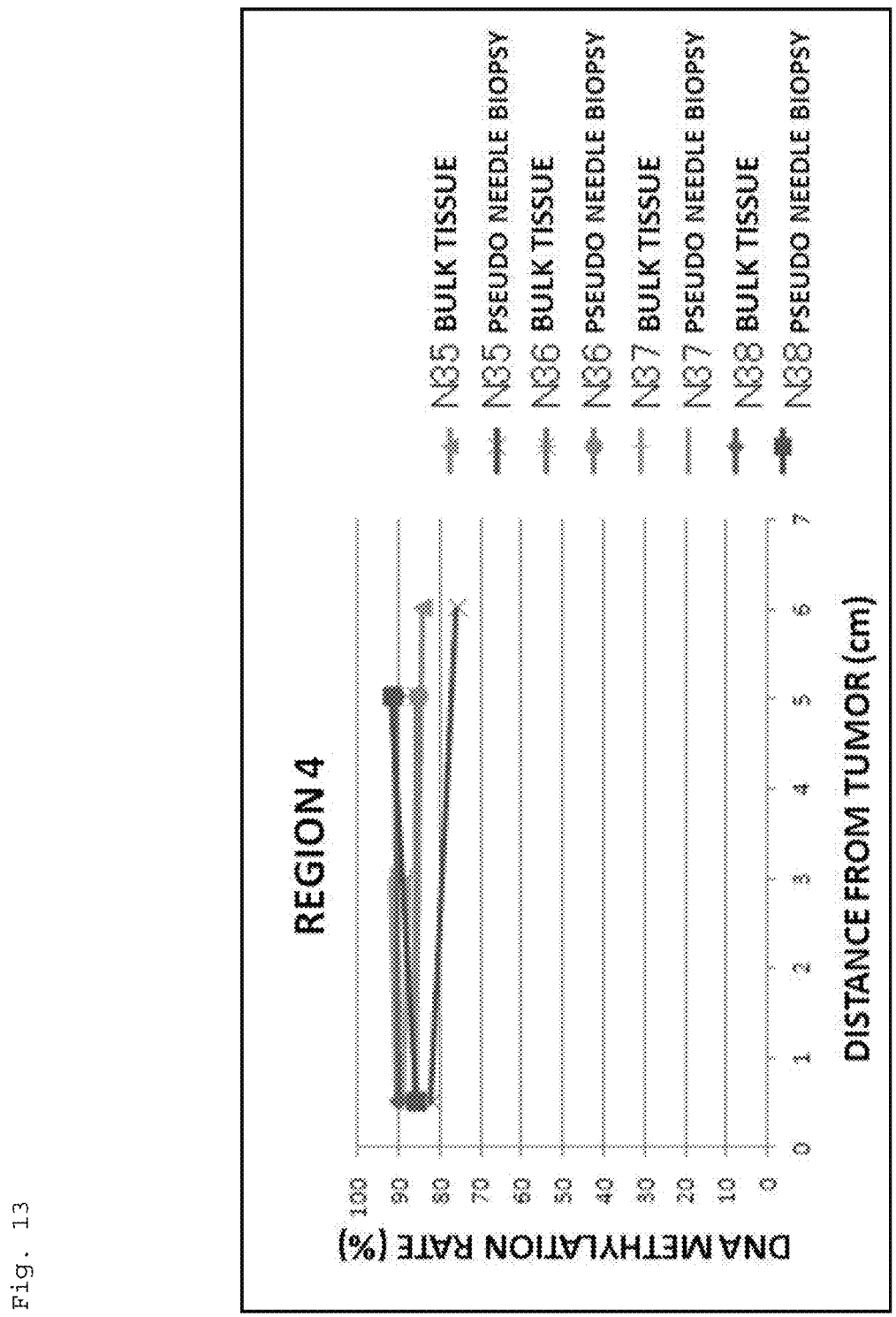
FIG. 13 shows a graph of the relationship between the DNA methylation level (rate) of Region 4 described in Table 4 and the distance from tumors (lesions of hepatocellular carcinoma) of sampled noncancerous liver tissues in noncancerous liver tissues (pseudo needle biopsy specimens or bulk tissues) sampled from the patients with HCC (N35 to N38) and prepared.

The results in the representative regions shown in FIGS. 12 and 13 indicated more than one sample obtained from the same partial hepatectomy specimen showed similar levels of DNA methylation rate regardless of whether pseudo needle biopsy specimens or bulk tissues independently of the distance from lesions of hepatocellular carcinoma.

Accordingly, since abnormal DNA methylation in 30 regions described in Table 4 reflects the cancer risk accumulated widely or uniformly in the liver. It was found that the criteria of methylation in 30 regions described in Table 4 (particularly, the 15 regions) in combination with the results shown in Example 5 was able to assess risk of hepatocellular carcinoma even using liver biopsy specimens having limitation in sampling site in clinical practice.

Example 7

<Validation 3 for Application of Criteria According to the Present Invention to Clinical Diagnosis>

If even specimens which were neither fixed in formalin nor embedded in paraffin, for example, bulk tissues can be assessed for risk of hepatocellular carcinoma using the regions (Regions: 1 to 5, 14, 16, 18, 19, 21, 23, 25 to 28 described in Table 4) at a similar level to the case using all 30 regions described in Table 4, such assessment is preferred in order to reduce the time and cost required for diagnosis, and is expected to easily spread in the department of clinical laboratory and the like. Thus, the methylation state in the 15 regions was analyzed for the pseudo needle biopsy specimens and the fresh frozen bulk tissues according to the same method as described in Example 6. A part of the obtained results (results of the cases N39 and N40) is shown in FIG. 14.

Figure 14:
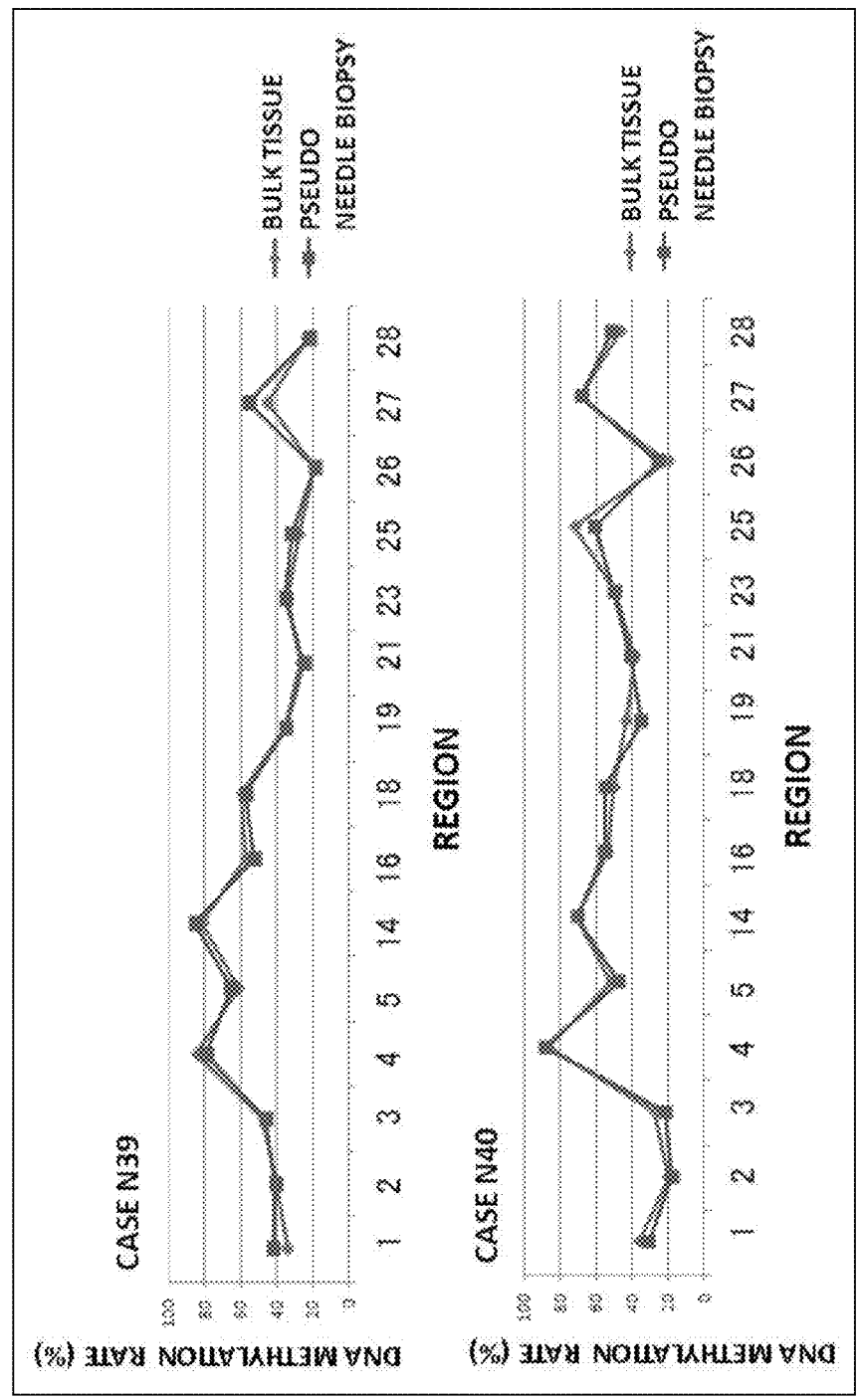
FIG. 14 shows graphs of the DNA methylation levels (rates) of Regions 1 to 5, 14, 16, 18, 19, 21, 23, and 25 to 28 described in Table 4 for noncancerous liver tissues (pseudo needle biopsy specimens or bulk tissues) sampled from the patients with HCC(N39 and N40) and prepared.

FIG. 14 showed that the DNA methylation statuses of the 15 regions were in good agreement with each other in the same case regardless of whether pseudo needle biopsy specimens or bulk tissues, and indicated that specimens which were neither fixed in formalin nor embedded in paraffin were able to be assessed for risk of hepatocellular carcinoma even using the 15 regions at a similar level to the case using all 30 regions described in Table 4.

Subsequently, bulk tissues of total 55 normal liver tissue samples (C1 to C35, C44 to C63) and total 57 noncancerous liver tissue samples (N1 to N34, N44 to N66) taken from partial hepatectomy specimens for HCC were analyzed for methylation status at the 15 regions. The obtained results are shown in FIG. 15.

Figure 15:
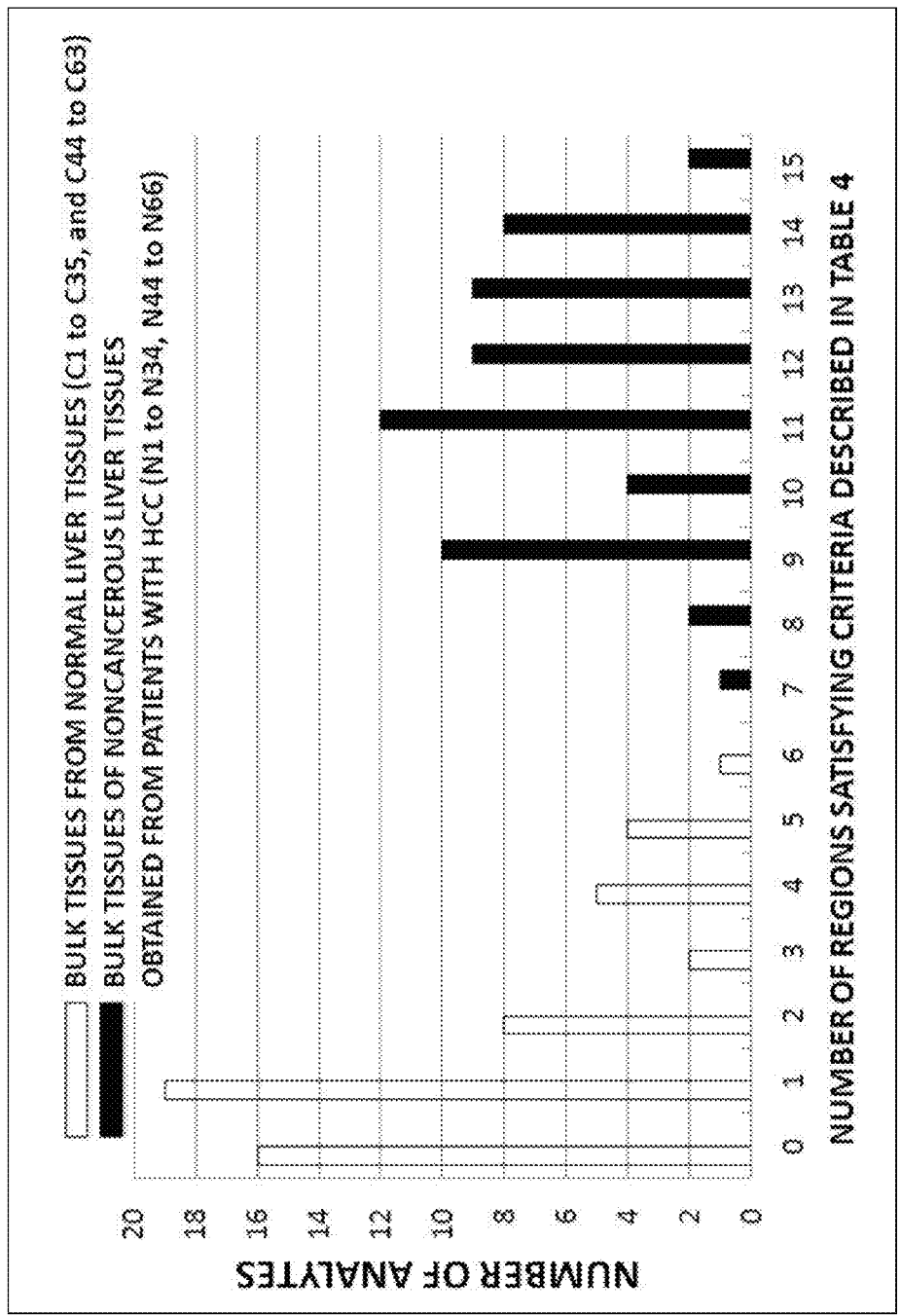
FIG. 15 shows a histogram of the relationship of the bulk tissues (C1 to C35, and C44 to C63) from normal liver tissues and the bulk tissues (N1 to N34, N44 to N66) from noncancerous liver tissues with the number of regions satisfying the criteria (criteria described in Table 4) for assessment of cancer risk for each bulk tissue among 15 regions (Regions 1 to 5, 14, 16, 18, 19, 21, 23, 25 to 28) described in Table 4. In the figure, white columns indicate Samples C and black columns indicates Samples N.

The results in FIG. 15 showed that when the liver tissues satisfying the criteria described in Table 4 for eight or more regions among the 15 regions were determined as high cancer risk, the bulk tissues of noncancerous liver tissues were able to be distinguished from the normal liver tissues with a sensitivity of 98% and a specificity of 98%. Therefore, it was found that the tissues which were neither fixed in formalin nor embedded in paraffin were also able to be assessed effectively for cancer risk by using the region. It was demonstrated that not only liver biopsy specimens which were sampled for histopathology and fixed in formalin and embedded in paraffin, but also liver tissues which were neither fixed in formalin nor embedded in paraffin (for example, surgically obtained bulk tissues) were able to be assessed for risk of hepatocellular carcinoma with high sensitivity and specificity even using the 15 regions instead of all 30 regions described in Table 4.

INDUSTRIAL APPLICABILITY

As described above, according to the present invention, the DNA methylation levels of the 45 CpG sites according to present invention or the DNA methylation levels in 30 regions described in Table 4 containing the sites can be detected to determine whether they are classified into a group of high cancer risk based on the methylation level.

Accordingly, the method of the present invention is useful for surveillance (follow-up) of patients with chronic hepatopathy such as chronic hepatitis and cirrhosis because the risk of hepatocellular carcinoma can be assessed with very high sensitivity and specificity.

According to the present invention, the risk of hepatocellular carcinoma can be assessed regardless of the conditions of liver tissues to be assessed, for example, with or without formalin fixation and paraffin embedding, and the distance from lesions of hepatocellular carcinoma, and therefore the present invention is very useful in clinical practice.

Furthermore, even using the 15 regions (Regions: 1 to 5, 14, 16, 18, 19, 21, 23, and 25 to 28 described in Table 4) instead of all 30 regions described in Table 4, the risk of hepatocellular carcinoma can be assessed with high sensitivity and specificity. Therefore, the present invention can further reduce the time and cost required for assessment, and in addition may spread widely in the department of clinical laboratory and the like.

SEQUENCE LISTING FREE TEXT

SEQ ID NOs: 1 to 90
<223> Artificially synthesized primer sequence

The invention claimed is:

1. A method for identifying a human subject with an increased risk of hepatocellular carcinoma, the method comprising:
   (a) preparing a sample of genomic DNA from liver tissue obtained from said human subject;
   (b) treating said genomic DNA sample with a bisulfite agent, then removing the bisulfite agent from the treated genomic DNA sample;
   (c) amplifying target DNA which contains the CpG site located at positions 26 and 27 of SEQ ID NO: 115, wherein said amplifying comprises:
      (i) providing an amplification reaction mixture comprising the bisulfite-treated genomic DNA; a forward primer comprising the nucleotide sequence of SEQ ID NO: 73; a biotin-labeled reverse primer comprising the nucleotide sequence of SEQ ID NO: 74; a thermostable DNA polymerase; and a plurality of free nucleotides comprising adenine, thymine, cytosine and guanine,
      (ii) heating the reaction mixture to a predetermined temperature, for a predetermined time, to separate the strands of the target DNA from each other,
      (iii) cooling the reaction mixture to predetermined temperatures, for predetermined times, under conditions to allow the forward and reverse primers to hybridize with their complementary sequences on the first and second strands of the target DNA, and to allow the polymerase to extend the primers, and
      (iv) repeating the heating and cooling steps at least 50 times;
   (d) dissociating the amplified, double-stranded DNA into single-stranded first and second strands, and selecting only the first or only the second strands;
   (e) performing an extension reaction with the selected strands, using a sequencing primer comprising the nucleotide sequence of SEQ ID NO: 75, to thereby generate pyrophosphoric acid, wherein said generation of pyrophosphoric acid results in the enzymatic emission of light;
   (f) determining the intensity of luminescence, and calculating the DNA methylation level (%) of the CpG site based on the following formula:

DNA Methylation Level (%)=Luminescence Intensity of Cytosine×100 /(Luminescence Intensity of Cytosine+Luminescence Intensity of Thymine); and (g) identifying the human subject as having an increased risk of hepatocellular carcinoma when the DNA methylation rate of the CpG site located at positions 26 and 27 of SEQ ID NO: 115 is increased in comparison to the DNA methylation rate of the CpG site in control genomic DNA samples from liver tissue obtained from human subjects without hepatocellular carcinoma.

2. The method according to claim 1, further comprising determining the DNA methylation level (%) of the CpG site located at positions 26 and 27 of SEQ ID NO: 117.

3. The method according to claim 2, further comprising determining the DNA methylation level (%) of the CpG site located at positions 26 and 27 of SEQ ID NO: 118.

4. The method according to claim 3, further comprising determining the DNA methylation level (%) of the CpG site located at positions 36 and 37 of SEQ ID NO: 118.

5. A method for identifying a human subject with an increased risk of hepatocellular carcinoma, the method comprising:
   (a) preparing a sample of genomic DNA from liver tissue obtained from said human subject;
   (b) treating said genomic DNA sample with a bisulfite agent, then removing the bisulfite agent from the treated genomic DNA sample;
   (c) amplifying target DNA, the amplified target DNA containing a plurality of CpG sites to be analyzed by pyrosequencing, wherein said amplifying comprises:
      (i) providing one or more amplification reaction mixtures each comprising the bisulfite-treated genomic DNA; a thermostable DNA polymerase; a plurality of free nucleotides comprising adenine, thymine, cytosine and guanine; and forward and reverse primers,
      (ii) heating the one or more reaction mixtures to a predetermined temperature, for a predetermined time, to separate the strands of the target DNA from each other,
      (iii) cooling the one or more reaction mixtures to predetermined temperatures, for predetermined times, under conditions to allow the forward and reverse primers to hybridize with their complementary sequences on the first and second strands of the target DNA, and to allow the polymerase to extend the primers, and
      (iv) repeating the heating and cooling steps at least 50 times;
   (d) dissociating the amplified, double-stranded DNA into single-stranded first and second strands, and selecting only the first or only the second strands;
   (e) extending strands selected from the one or more amplification reactions in step (d) using sequencing primers, to thereby generate pyrophosphoric acid, wherein said generation of pyrophosphoric acid results in the enzymatic emission of light;

(f) determining the intensity of luminescence, and calculating the DNA methylation level (%) of the CpG site based on the following formula:

DNA Methylation Level (%)=Luminescence Intensity of Cytosine×100/(Luminescence Intensity of Cytosine+Luminescence Intensity of Thymine); and (g) identifying the human subject as having an increased risk of hepatocellular carcinoma by comparing the DNA methylation rate of each of the CpG sites in said plurality of CpG sites to cut-off values for distinguishing between normal liver tissue samples and noncancerous liver tissue samples from patients with hepatocellular carcinoma, wherein said plurality of CpG sites to be analyzed comprises the CpG sites located at positions 26 and 27 of SEQ ID NO: 115, at positions 26 and 27 of SEQ ID NO: 117, and at positions 26, 27, 36 and 37 of SEQ ID NO: 118, and wherein said analysis of said plurality of CpG sites by pyrosequencing comprises using the following primer sets (1)-(3):

(1) a forward primer comprising the nucleotide sequence of SEQ ID NO: 73, a biotin-labeled reverse primer comprising the nucleotide sequence of SEQ ID NO: 74, and a sequencing primer comprising the nucleotide sequence of SEQ ID NO: 75, (2) a forward primer comprising the nucleotide sequence of SEQ ID NO: 79, a biotin-labeled reverse primer comprising the nucleotide sequence of SEQ ID NO: 80, and a sequencing primer comprising the nucleotide sequence of SEQ ID NO: 81, and (3) a forward primer comprising the nucleotide sequence of SEQ ID NO: 82, a biotin-labeled reverse primer comprising the nucleotide sequence of SEQ ID NO: 83, and a sequencing primer comprising the nucleotide sequence of SEQ ID NO: 84.

6. The method according to claim 5, wherein the plurality of CpG sites to be analyzed further comprises the CpG sites located at positions 26 and 27 of SEQ ID NO: 91, at positions 16, 17, 26, 27, 31 and 32 of SEQ ID NO: 92, at positions 26, 27, 37 and 38 of SEQ ID NO: 93, at positions 26 and 27 of SEQ ID NO: 94, at positions 20, 21, 26, 27, 29 and 30 of SEQ ID NO: 95, at positions 22, 23, 26, 27, 28, 29, 31 and 32 of SEQ ID NO: 104, at positions 26 and 27 of SEQ ID NO: 106, at positions 26, 27, 34 and 35 of SEQ ID NO: 108, at positions 26 and 27 of SEQ ID NO: 109, at positions 26 and 27 of SEQ ID NO: 111, at positions 26 and 27 of SEQ ID NO: 113, and at positions 26 and 27 of SEQ ID NO:116; and wherein the analysis of said plurality of CpG sites by pyrosequencing further comprises using the following primer sets (4)-(15):

(4) a forward primer comprising the nucleotide sequence of SEQ ID NO: 1, a biotin-labeled reverse primer comprising the nucleotide sequence of SEQ ID NO: 2, and a sequencing primer comprising the nucleotide sequence of SEQ ID NO: 3, (5) a forward primer comprising the nucleotide sequence of SEQ ID NO: 4, a biotin-labeled reverse primer comprising the nucleotide sequence of SEQ ID NO: 5, and a sequencing primer comprising the nucleotide sequence of SEQ ID NO: 6, (6) a forward primer comprising the nucleotide sequence of SEQ ID NO: 7, a biotin-labeled reverse primer comprising the nucleotide sequence of SEQ ID NO: 8, and a sequencing primer comprising the nucleotide sequence of SEQ ID NO: 9, (7) a forward primer comprising the nucleotide sequence of SEQ ID NO: 10, a biotin-labeled reverse primer comprising the nucleotide sequence of SEQ ID NO: 11, and a sequencing primer comprising the nucleotide sequence of SEQ ID NO: 12, (8) a forward primer comprising the nucleotide sequence of SEQ ID NO: 13, a biotin-labeled reverse primer comprising the nucleotide sequence of SEQ ID NO: 14, and a sequencing primer comprising the nucleotide sequence of SEQ ID NO: 15, (9) a forward primer comprising the nucleotide sequence of SEQ ID NO: 40, a biotin-labeled reverse primer comprising the nucleotide sequence of SEQ ID NO: 41, and a sequencing primer comprising the nucleotide sequence of SEQ ID NO: 42,

(10) a forward primer comprising the nucleotide sequence of SEQ ID NO: 46, a biotin-labeled reverse primer comprising the nucleotide sequence of SEQ ID NO: 47, and a sequencing primer comprising the nucleotide sequence of SEQ ID NO: 48,

(11) a forward primer comprising the nucleotide sequence of SEQ ID NO: 52, a biotin-labeled reverse primer comprising the nucleotide sequence of SEQ ID NO: 53, and a sequencing primer comprising the nucleotide sequence of SEQ ID NO: 54,

(12) a forward primer comprising the nucleotide sequence of SEQ ID NO: 55, a biotin-labeled reverse primer comprising the nucleotide sequence of SEQ ID NO: 56, and a sequencing primer comprising the nucleotide sequence of SEQ ID NO: 57,

(13) a forward primer comprising the nucleotide sequence of SEQ ID NO: 61, a biotin-labeled reverse primer comprising the nucleotide sequence of SEQ ID NO: 62, and a sequencing primer comprising the nucleotide sequence of SEQ ID NO: 63,

(14) a forward primer comprising the nucleotide sequence of SEQ ID NO: 67, a biotin-labeled reverse primer comprising the nucleotide sequence of SEQ ID NO: 68, and a sequencing primer comprising the nucleotide sequence of SEQ ID NO: 69; and

(15) a forward primer comprising the nucleotide sequence of SEQ ID NO: 76, a biotin-labeled reverse primer comprising the nucleotide sequence of SEQ ID NO: 77, and a sequencing primer comprising the nucleotide sequence of SEQ ID NO: 78.

7. The method according to claim 6, wherein the plurality of CpG sites to be analyzed further comprises the CpG sites located at positions 26 and 27 of SEQ ID NO: 96, at positions 26 and 27 of SEQ ID NO: 97, at positions 26 and 27 of SEQ ID NO: 98, at positions 26, 27, 30 and 31 of SEQ ID NO: 99, at positions 26 and 27 of SEQ ID NO: 100, at positions 26, 27, 43 and 44 of SEQ ID NO: 101, at positions 26 and 27 of SEQ ID NO: 102, at positions 26 and 27 of SEQ ID NO: 103, at positions 26 and 27 of SEQ ID NO: 105, at positions 26 and 27 of SEQ ID NO: 107, at positions 26, 27, 29 and 30 of SEQ ID NO: 110, at positions 26, 27, 36 and 37 of SEQ ID NO: 112, at positions 26 and 27 of SEQ ID NO: 114, at positions 26 and 27 of SEQ ID NO: 119, and at positions 26, 27, 31 and 32 of SEQ ID NO: 120; and wherein the analysis of said plurality of CpG sites by pyrosequencing further comprises using the following primer sets (16)-(30):

(16) a forward primer comprising the nucleotide sequence of SEQ ID NO: 16, a biotin-labeled reverse primer comprising the nucleotide sequence of SEQ ID NO: 17, and a sequencing primer comprising the nucleotide sequence of SEQ ID NO: 18,
(17) a forward primer comprising the nucleotide sequence of SEQ ID NO: 19, a biotin-labeled reverse primer comprising the nucleotide sequence of SEQ ID NO: 20, and a sequencing primer comprising the nucleotide sequence of SEQ ID NO: 21,
(18) a forward primer comprising the nucleotide sequence of SEQ ID NO: 22, a biotin-labeled reverse primer comprising the nucleotide sequence of SEQ ID NO: 23, and a sequencing primer comprising the nucleotide sequence of SEQ ID NO: 24,
(19) a forward primer comprising the nucleotide sequence of SEQ ID NO: 25, a biotin-labeled reverse primer comprising the nucleotide sequence of SEQ ID NO: 26, and a sequencing primer comprising the nucleotide sequence of SEQ ID NO: 27,
(20) a forward primer comprising the nucleotide sequence of SEQ ID NO: 28, a biotin-labeled reverse primer comprising the nucleotide sequence of SEQ ID NO: 29, and a sequencing primer comprising the nucleotide sequence of SEQ ID NO: 30,
(21) a forward primer comprising the nucleotide sequence of SEQ ID NO: 31, a biotin-labeled reverse primer comprising the nucleotide sequence of SEQ ID NO: 32, and a sequencing primer comprising the nucleotide sequence of SEQ ID NO: 33,
(22) a forward primer comprising the nucleotide sequence of SEQ ID NO: 34, a biotin-labeled reverse primer comprising the nucleotide sequence of SEQ ID NO: 35, and a sequencing primer comprising the nucleotide sequence of SEQ ID NO: 36,
(23) a forward primer comprising the nucleotide sequence of SEQ ID NO: 37, a biotin-labeled reverse primer comprising the nucleotide sequence of SEQ ID NO: 38, and a sequencing primer comprising the nucleotide sequence of SEQ ID NO: 39,
(24) a forward primer comprising the nucleotide sequence of SEQ ID NO: 43, a biotin-labeled reverse primer comprising the nucleotide sequence of SEQ ID NO: 44, and a sequencing primer comprising the nucleotide sequence of SEQ ID NO: 45,
(25) a forward primer comprising the nucleotide sequence of SEQ ID NO: 49, a biotin-labeled reverse primer comprising the nucleotide sequence of SEQ ID NO: 50, and a sequencing primer comprising the nucleotide sequence of SEQ ID NO: 51,
(26) a forward primer comprising the nucleotide sequence of SEQ ID NO: 58, a biotin-labeled reverse primer comprising the nucleotide sequence of SEQ ID NO: 59, and a sequencing primer comprising the nucleotide sequence of SEQ ID NO: 60,
(27) a forward primer comprising the nucleotide sequence of SEQ ID NO: 64, a biotin-labeled reverse primer comprising the nucleotide sequence of SEQ ID NO: 65, and a sequencing primer comprising the nucleotide sequence of SEQ ID NO: 66,
(28) a forward primer comprising the nucleotide sequence of SEQ ID NO: 70, a biotin-labeled reverse primer comprising the nucleotide sequence of SEQ ID NO: 71, and a sequencing primer comprising the nucleotide sequence of SEQ ID NO: 72,
(29) a forward primer comprising the nucleotide sequence of SEQ ID NO: 85, a biotin-labeled reverse primer comprising the nucleotide sequence of SEQ ID NO: 86, and a sequencing primer comprising the nucleotide sequence of SEQ ID NO: 87, and
(30) a forward primer comprising the nucleotide sequence of SEQ ID NO: 88, a biotin-labeled reverse primer comprising the nucleotide sequence of SEQ ID NO: 89, and a sequencing primer comprising the nucleotide sequence of SEQ ID NO: 90.

* * * * *

```
SEQUENCE LISTING

<160> NUMBER OF SEQ ID NOS: 121

<210> SEQ ID NO 1
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 1
gttgggtggg gtagaatt                                                    18

<210> SEQ ID NO 2
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 2
aaacaaaacc taacaaaata cc                                               22

<210> SEQ ID NO 3
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 3
ggattaggat tgtgggatg                                                   19
```

-continued

```
<210> SEQ ID NO 4
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 4
gtagtgattt gggtagtagg gat                                              23

<210> SEQ ID NO 5
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 5
ctaatacttc tctcacccac aca                                              23

<210> SEQ ID NO 6
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 6
gaaatttgta gttgggtaa                                                   20

<210> SEQ ID NO 7
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 7
aaaagtggtt atggtttggg tata                                             24

<210> SEQ ID NO 8
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 8
tattccccca cctcccaata a                                                21

<210> SEQ ID NO 9
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 9 gtttttagg ttagagtagg                                                   20

<210> SEQ ID NO 10
<211> LENGTH: 28
<212> TYPE: DNA
<213> ORGANISM: Artificial Sequence
<220> FEATURE:
<223> OTHER INFORMATION: Artificially synthesized primer sequence
```

```
<400> SEQUENCE: 10
agggttatta tataaattga ggaatgta                                28

<210> SEQ ID NO 11
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 11
acataaaaac aaacccctcc at                                     22

<210> SEQ ID NO 12
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 12
tgtaggtatt tagtgtgtga                                        20

<210> SEQ ID NO 13
<211> LENGTH: 26
<212> TYPE: DNA
<213> ORGANISM: Artificial Sequence
<220> FEATURE:
<223> OTHER INFORMATION: Artificially synthesized primer sequence

<400> SEQUENCE: 13
agggtagagg ttttttttttt ttatag                                26

<210> SEQ ID NO 14
<211> LENGTH: 26
<212> TYPE: DNA
<213> ORGANISM: Artificial Sequence
<220> FEATURE:
<223> OTHER INFORMATION: Artificially synthesized primer sequence

<400> SEQUENCE: 14
atcaacataa ccaaaaccta aactta                                 26

<210> SEQ ID NO 15
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 15
tttatagatt atattatggg                                        20

<210> SEQ ID NO 16
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 16
gttgttatgg gtagtgattg tgta                                   24

<210> SEQ ID NO 17
<211> LENGTH: 26
```

```
<212> TYPE: DNA
<213> ORGANISM: Artificial Sequence
<220> FEATURE:
<223> OTHER INFORMATION: Artificially synthesized primer sequence

<400> SEQUENCE: 17
ttcaactcta ttcccataaa ctacaa                                          26

<210> SEQ ID NO 18
<211> LENGTH: 16
<212> TYPE: DNA
<213> ORGANISM: Artificial Sequence
<220> FEATURE:
<223> OTHER INFORMATION: Artificially synthesized primer sequence

<400> SEQUENCE: 18
ttatttgggt ttaggg                                                     16

<210> SEQ ID NO 19
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 19 gtttttagg tgttggttga ttat                                             24

<210> SEQ ID NO 20
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 20
aacccaaact aaatcactct aatac                                           25

<210> SEQ ID NO 21
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 21
taggattagg agtaggaa                                                   18

<210> SEQ ID NO 22
<211> LENGTH: 26
<212> TYPE: DNA
<213> ORGANISM: Artificial Sequence
<220> FEATURE:
<223> OTHER INFORMATION: Artificially synthesized primer sequence

<400> SEQUENCE: 22
tatgaggttt agagaggttg ttatgt                                          26

<210> SEQ ID NO 23
<211> LENGTH: 26
<212> TYPE: DNA
<213> ORGANISM: Artificial Sequence
<220> FEATURE:
<223> OTHER INFORMATION: Artificially synthesized primer sequence

<400> SEQUENCE: 23
```
ctactttacc aataaacaac ctacat                                    26

<210> SEQ ID NO 24
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 24
tggttagtag gaaagaat                                             18

<210> SEQ ID NO 25
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 25 ttagggttg ttttggatta tatta                                      25

<210> SEQ ID NO 26
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 26
ttaaatccac tcaaatccca ctact                                     25

<210> SEQ ID NO 27
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 27
ttagttgtgg aaaggatata                                           20

<210> SEQ ID NO 28
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 28
gtagtagatg gattttttg agga                                       24

<210> SEQ ID NO 29
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 29
ccaaaatatc cttacacaat aatcc                                     25

<210> SEQ ID NO 30
<211> LENGTH: 20
<212> TYPE: DNA
<213> ORGANISM: Artificial Sequence

```
<220> FEATURE:
<223> OTHER INFORMATION: Artificially synthesized primer sequence

<400> SEQUENCE: 30
attttttttt taattaagtg                                              20

<210> SEQ ID NO 31
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 31
ggtagattat ttgaggttag gagtt                                        25

<210> SEQ ID NO 32
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 32
caaatcattt tataataatc cctttac                                      27

<210> SEQ ID NO 33
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 33
aaggttgaag taggagaat                                               19

<210> SEQ ID NO 34
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 34
tggttaggag tgtttggaag                                              20

<210> SEQ ID NO 35
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 35
atcctaccta atccacaaac tac                                          23

<210> SEQ ID NO 36
<211> LENGTH: 15
<212> TYPE: DNA
<213> ORGANISM: Artificial Sequence
<220> FEATURE:
<223> OTHER INFORMATION: Artificially synthesized primer sequence

<400> SEQUENCE: 36
ggagtgtttg gaagg                                                   15
```

```
<210> SEQ ID NO 37
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 37
gtagggtatt gtttaggttg agtg                                          24

<210> SEQ ID NO 38
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 38
ccttcctcct aaatctaact caaa                                          24

<210> SEQ ID NO 39
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 39
ggtattgttt aggttgagtg                                               20

<210> SEQ ID NO 40
<211> LENGTH: 26
<212> TYPE: DNA
<213> ORGANISM: Artificial Sequence
<220> FEATURE:
<223> OTHER INFORMATION: Artificially synthesized primer sequence

<400> SEQUENCE: 40
ttatagaagg gaagggagtt ttgtaa                                        26

<210> SEQ ID NO 41
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 41
ccactcacaa aacataacct atttctc                                       27

<210> SEQ ID NO 42
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 42
taggtattgg tttttttgg                                                18

<210> SEQ ID NO 43
<211> LENGTH: 27
<212> TYPE: DNA
<213> ORGANISM: Artificial Sequence
<220> FEATURE:
<223> OTHER INFORMATION: Artificially synthesized primer sequence
```

<400> SEQUENCE: 43
ttgagtgtta gttaggtttt tagtaag                              27

<210> SEQ ID NO 44
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 44
caaataaaat actcctttca tctatatc                             28

<210> SEQ ID NO 45
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 45 ggttttagt aaggagat                                         18

<210> SEQ ID NO 46
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 46
tattgaatta taggtgtaga agggagtta                            29

<210> SEQ ID NO 47
<211> LENGTH: 26
<212> TYPE: DNA
<213> ORGANISM: Artificial Sequence
<220> FEATURE:
<223> OTHER INFORMATION: Artificially synthesized primer sequence

<400> SEQUENCE: 47
atctttaaac caaaacaacc actttc                               26

<210> SEQ ID NO 48
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 48
tagaagagtt tgattagg                                        18

<210> SEQ ID NO 49
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 49
gggagggttt gtagttaagg tat                                  23

<210> SEQ ID NO 50

-continued

```
<210> SEQ ID NO 51
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 50
acaaataaca ccccatctcc ta                                              22

<210> SEQ ID NO 51
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 51
gggagggttt gtagttaag                                                  19

<210> SEQ ID NO 52
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 52
agaagaaaga aatttttaa tggagaatat                                       30

<210> SEQ ID NO 53
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 53
ctttccctac caccttatat ctacctattt                                      30

<210> SEQ ID NO 54
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 54 gttttttta tttatagatg                                                  20

<210> SEQ ID NO 55
<211> LENGTH: 26
<212> TYPE: DNA
<213> ORGANISM: Artificial Sequence
<220> FEATURE:
<223> OTHER INFORMATION: Artificially synthesized primer sequence

<400> SEQUENCE: 55
agttaaaaat atagttgggt tgaaat                                          26

<210> SEQ ID NO 56
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 56
```
aattccctaa cttaacactc taact                                      25

<210> SEQ ID NO 57
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 57
ttttatggtt agtatggtg                                             19

<210> SEQ ID NO 58
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 58
ggagtttata aagggagg                                              18

<210> SEQ ID NO 59
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 59
tccttctact acaacttcct aaat                                       24

<210> SEQ ID NO 60
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 60
agttaggttg gtatttttta                                            20

<210> SEQ ID NO 61
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 61
aaggttttgt gagttaatga aa                                         22

<210> SEQ ID NO 62
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 62
caccctactc aaataaactc taaa                                       24

<210> SEQ ID NO 63
<211> LENGTH: 19
<212> TYPE: DNA

```
<213> ORGANISM: Artificial Sequence
<220> FEATURE:
<223> OTHER INFORMATION: Artificially synthesized primer sequence

<400> SEQUENCE: 63
ttatttgttt gtgaaatag                                              19

<210> SEQ ID NO 64
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 64
gggtgtttgt aattttagtt atttagga                                    28

<210> SEQ ID NO 65
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 65
cccaatttat caaaaatcaa cacca                                       25

<210> SEQ ID NO 66
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 66
ggagattaag gtaggagaa                                              19

<210> SEQ ID NO 67
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 67
agattttatt ataattgggg tagta                                       25

<210> SEQ ID NO 68
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 68
aaaaacccca taaactaact ct                                          22

<210> SEQ ID NO 69
<211> LENGTH: 16
<212> TYPE: DNA
<213> ORGANISM: Artificial Sequence
<220> FEATURE:
<223> OTHER INFORMATION: Artificially synthesized primer sequence

<400> SEQUENCE: 69
aggagtgttg taggtt                                                 16
```

<210> SEQ ID NO 70
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 70
agaattggaa gatggttgta ttgt                                          24

<210> SEQ ID NO 71
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 71
ccaaactata ttctcctcct taca                                          24

<210> SEQ ID NO 72
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 72
tttttgggat tttttaat                                                 18

<210> SEQ ID NO 73
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 73
tattggagaa gagggttgtg tttatat                                       27

<210> SEQ ID NO 74
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 74
cccccaaact cacactaccc tac                                           23

<210> SEQ ID NO 75
<211> LENGTH: 16
<212> TYPE: DNA
<213> ORGANISM: Artificial Sequence
<220> FEATURE:
<223> OTHER INFORMATION: Artificially synthesized primer sequence

<400> SEQUENCE: 75
gaggatggtg ataagt                                                   16

<210> SEQ ID NO 76
<211> LENGTH: 22
<212> TYPE: DNA
<213> ORGANISM: Artificial Sequence
<220> FEATURE:

<223> OTHER INFORMATION: Artificially synthesized primer sequence

<400> SEQUENCE: 76
agtagtggtg aagtgattg gt                                             22

<210> SEQ ID NO 77
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 77
cccaacccct actcaaactt ct                                            22

<210> SEQ ID NO 78
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 78
aagtgttatt tggttattat                                               20

<210> SEQ ID NO 79
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 79
agttggtttt gagggaaagt agt                                           23

<210> SEQ ID NO 80
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 80
ctccaccaaa aaatactacc tcc                                           23

<210> SEQ ID NO 81
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 81
ggttttgagg gaaagtag                                                 18

<210> SEQ ID NO 82
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 82
taggttttat agttaggagg gtagg                                         25

```
<210> SEQ ID NO 83
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 83
cccaaacacc caacaaattc                                                   20

<210> SEQ ID NO 84
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 84
ttttatagtt aggagggta                                                    19

<210> SEQ ID NO 85
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 85
agtttaagtt ttggtgagtg tttg                                              24

<210> SEQ ID NO 86
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 86
tcacctaata aaaccctac cac                                                23

<210> SEQ ID NO 87
<211> LENGTH: 16
<212> TYPE: DNA
<213> ORGANISM: Artificial Sequence
<220> FEATURE:
<223> OTHER INFORMATION: Artificially synthesized primer sequence

<400> SEQUENCE: 87
gggagggagt taattt                                                       16

<210> SEQ ID NO 88
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 88
ttggggtggg tttaggtgat a                                                 21

<210> SEQ ID NO 89
<211> LENGTH: 23
<212> TYPE: DNA
<213> ORGANISM: Artificial Sequence
<220> FEATURE:
<223> OTHER INFORMATION: Artificially synthesized primer sequence
```

<400> SEQUENCE: 89
ttcctcccaa taacctccct aaa                                    23

<210> SEQ ID NO 90
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 90
gggtaagaag ttattatagg                                        20

<210> SEQ ID NO 91
<211> LENGTH: 50
<212> TYPE: DNA
<213> ORGANISM: Homo sapiens

<400> SEQUENCE: 91
tgtgggatgc ttcccacccc gcccccgccc cgggccgccg cccgccgccc        50

<210> SEQ ID NO 92
<211> LENGTH: 50
<212> TYPE: DNA
<213> ORGANISM: Homo sapiens

<400> SEQUENCE: 92
gggcaacctt ccctgcgtca tctcccgggg cgggcggccc tgtgtgggtg        50

<210> SEQ ID NO 93
<211> LENGTH: 50
<212> TYPE: DNA
<213> ORGANISM: Homo sapiens

<400> SEQUENCE: 93
gtccttctcg cgcctcccag gccagcgcag gggtcccgct tcgtcccgg         50

<210> SEQ ID NO 94
<211> LENGTH: 50
<212> TYPE: DNA
<213> ORGANISM: Homo sapiens

<400> SEQUENCE: 94
actctggaag agagaccaag aatgccggta cccagtgtgt gacgacagcc        50

<210> SEQ ID NO 95
<211> LENGTH: 50
<212> TYPE: DNA
<213> ORGANISM: Homo sapiens

<400> SEQUENCE: 95
tagaccacat catgggccac ggtggcggcg gggcagcacc cccgggcgcc        50

<210> SEQ ID NO 96
<211> LENGTH: 50
<212> TYPE: DNA
<213> ORGANISM: Homo sapiens

<400> SEQUENCE: 96
actcgcccca cctgggctca gggcccgggg tccactcatg ttgctgactt        50

<210> SEQ ID NO 97
<211> LENGTH: 50

```
<212> TYPE: DNA
<213> ORGANISM: Homo sapiens

<400> SEQUENCE: 97
agcacaggat caggagcagg aagcccgggg tctcccattt cagagagcag      50

<210> SEQ ID NO 98
<211> LENGTH: 50
<212> TYPE: DNA
<213> ORGANISM: Homo sapiens

<400> SEQUENCE: 98
acactggtta gcaggaaaga acacccgggt ttgtgtgcgc accggtctat      50

<210> SEQ ID NO 99
<211> LENGTH: 50
<212> TYPE: DNA
<213> ORGANISM: Homo sapiens

<400> SEQUENCE: 99
agctgtggaa aggacacagc ctcctcgccc gggcaggagc gcccgcgggg      50

<210> SEQ ID NO 100
<211> LENGTH: 50
<212> TYPE: DNA
<213> ORGANISM: Homo sapiens

<400> SEQUENCE: 100 ttcccctttta accaagtggg tctcccgaag gccccgggga ttattgtgta     50

<210> SEQ ID NO 101
<211> LENGTH: 50
<212> TYPE: DNA
<213> ORGANISM: Homo sapiens

<400> SEQUENCE: 101
ctcgggaagg ctgaagcagg agaatcgctt gagcccggga ggcggaggtt      50

<210> SEQ ID NO 102
<211> LENGTH: 50
<212> TYPE: DNA
<213> ORGANISM: Homo sapiens

<400> SEQUENCE: 102
tggtggcccg gcgtgcctgg aaggccgggg tgccccgggc agaggctggg      50

<210> SEQ ID NO 103
<211> LENGTH: 50
<212> TYPE: DNA
<213> ORGANISM: Homo sapiens

<400> SEQUENCE: 103
cgcgagagcg cgcagggcat tgcctcggtt gagtgcgccc gggtgcgcag      50

<210> SEQ ID NO 104
<211> LENGTH: 50
<212> TYPE: DNA
<213> ORGANISM: Homo sapiens

<400> SEQUENCE: 104
acaggcactg gctctctggc ccgggcgcgc cgtccaggag gcgcgtgttc      50

<210> SEQ ID NO 105
```

<211> LENGTH: 50
<212> TYPE: DNA
<213> ORGANISM: Homo sapiens

<400> SEQUENCE: 105
cagccaggcc cccagcaagg agacccgggc tccccaggtg aagttcctta         50

<210> SEQ ID NO 106
<211> LENGTH: 50
<212> TYPE: DNA
<213> ORGANISM: Homo sapiens

<400> SEQUENCE: 106
tttctagaag agcctgatta ggccccggga aagtggctgt tttggtttaa         50

<210> SEQ ID NO 107
<211> LENGTH: 50
<212> TYPE: DNA
<213> ORGANISM: Homo sapiens

<400> SEQUENCE: 107
ttgcagccaa ggcatttatg ccccccgggg ctcccttctg tcatccctcc         50

<210> SEQ ID NO 108
<211> LENGTH: 50
<212> TYPE: DNA
<213> ORGANISM: Homo sapiens

<400> SEQUENCE: 108
cccttctcat ttacagatga agaatcggag gcccgggtag gggaggagac         50

<210> SEQ ID NO 109
<211> LENGTH: 50
<212> TYPE: DNA
<213> ORGANISM: Homo sapiens

<400> SEQUENCE: 109
agcatggtgc accccctacc actcccggga caggatgcaa aagaggctcc         50

<210> SEQ ID NO 110
<211> LENGTH: 50
<212> TYPE: DNA
<213> ORGANISM: Homo sapiens

<400> SEQUENCE: 110
gcccgcccgg ctggcatccc ccagccgccg ccagccccgc cgaggggagc         50

<210> SEQ ID NO 111
<211> LENGTH: 50
<212> TYPE: DNA
<213> ORGANISM: Homo sapiens

<400> SEQUENCE: 111
aaaaccactt gcttgtgaaa cagcccgggg tgttgctgaa tcccaccagg         50

<210> SEQ ID NO 112
<211> LENGTH: 50
<212> TYPE: DNA
<213> ORGANISM: Homo sapiens

<400> SEQUENCE: 112
actcaggaga ctaaggcagg agaatcgctt gaacccgggt ggtggaggtt         50

<210> SEQ ID NO 113
<211> LENGTH: 50
<212> TYPE: DNA
<213> ORGANISM: Homo sapiens

<400> SEQUENCE: 113
tggggcagca ggagtgctgt aggcccggga catcttcagt gacaggtgtc        50

<210> SEQ ID NO 114
<211> LENGTH: 50
<212> TYPE: DNA
<213> ORGANISM: Homo sapiens

<400> SEQUENCE: 114 ctcccctgg accccccaa cctcccgggt cctgggtgct gagggtaggg           50

<210> SEQ ID NO 115
<211> LENGTH: 50
<212> TYPE: DNA
<213> ORGANISM: Homo sapiens

<400> SEQUENCE: 115
ccccaccgag gacggcgaca agccccgggt gctctacagc ctggagttca        50

<210> SEQ ID NO 116
<211> LENGTH: 50
<212> TYPE: DNA
<213> ORGANISM: Homo sapiens

<400> SEQUENCE: 116
aagtgccatc tggccatcac tttcccgggg acctgggagc tgggcagggg        50

<210> SEQ ID NO 117
<211> LENGTH: 50
<212> TYPE: DNA
<213> ORGANISM: Homo sapiens

<400> SEQUENCE: 117
cagctcccct gaggtgaggc ccccccgggg aagctttgcg cacccgcccg        50

<210> SEQ ID NO 118
<211> LENGTH: 50
<212> TYPE: DNA
<213> ORGANISM: Homo sapiens

<400> SEQUENCE: 118
ctgccctgca ctgtcctcca agggccgcta ggtggcgctc ccgcccttcc        50

<210> SEQ ID NO 119
<211> LENGTH: 50
<212> TYPE: DNA
<213> ORGANISM: Homo sapiens

<400> SEQUENCE: 119
gagcccctcg ggagggagtc aatcccgggt acacggctgg gcgccgtggc        50

<210> SEQ ID NO 120
<211> LENGTH: 50
<212> TYPE: DNA
<213> ORGANISM: Homo sapiens

<400> SEQUENCE: 120
agacgtcacc acagggagcc cgggccgagg cgcacgcctc tgatttcctg        50

```
<210> SEQ ID NO 121
<211> LENGTH: 18
<212> TYPE: DNA
<213> ORGANISM: Artificial Sequence
<220> FEATURE:
<223> OTHER INFORMATION: Dispensation order(order in which dNTP is
      added)

<400> SEQUENCE: 121
atgatcgtag tcagtcgg                                                  18
```